US011246706B2

(12) United States Patent
Dale et al.

(10) Patent No.: US 11,246,706 B2
(45) Date of Patent: Feb. 15, 2022

(54) TRANSCATHETER MITRAL VALVE STENT FRAMES

(71) Applicant: St. Jude Medical, Cardiology Division, Inc., St. Paul, MN (US)

(72) Inventors: Theodore Paul Dale, Corcoran, MN (US); Andrea N. Para, Centennial, CO (US); Gaurav Satam, Falcon Heights, MN (US); Jason Diedering, Minneapolis, MN (US); Thomas Mark Benson, Minneapolis, MN (US); Saravana B. Kumar, Minnetonka, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 87 days.

(21) Appl. No.: 16/391,414

(22) Filed: Apr. 23, 2019

(65) Prior Publication Data

US 2019/0247189 A1    Aug. 15, 2019

Related U.S. Application Data

(62) Division of application No. 14/662,464, filed on Mar. 19, 2015, now abandoned.
(Continued)

(51) Int. Cl.
*A61F 2/24* (2006.01)
*A61F 2/848* (2013.01)

(52) U.S. Cl.
CPC .......... *A61F 2/2442* (2013.01); *A61F 2/2409* (2013.01); *A61F 2/2418* (2013.01);
(Continued)

(58) Field of Classification Search
CPC ........ A61F 2/2412; A61F 2/2418; A61F 2/24; A61F 2/2409; A61F 2/243; A61F 2/2436;
(Continued)

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| CA | 2682564 A1 | 10/2008 |
| DE | 19857887 A1 | 7/2000 |

(Continued)

OTHER PUBLICATIONS

Australian Search Report for Application No. 2015236516, dated Jul. 26, 2019, 1 pg.
(Continued)

*Primary Examiner* — Seema Mathew
(74) *Attorney, Agent, or Firm* — Lerner, David, Littenberg, Krumholz & Mentlik, LLP

(57) ABSTRACT

A prosthetic heart valve may include a stent having an inflow end, an outflow end, a collapsed condition, and an expanded condition. The prosthetic valve may also include a collapsible and expandable valve assembly disposed within the stent and having a plurality of leaflets. The prosthetic valve and/or stent may include features to anchor the prosthetic valve to a native valve annulus and to seal the prosthetic valve with respect to the native valve annulus, such as planar and/or nonplanar annular sealing members coupled to ends of the stent. The stent may include one or more circumferential rows of anchor members or hooks extending radially outwardly from the stent. These hooks may be configured to extend in a particular direction when the stent is in the collapsed condition to facilitate resheathing of the stent if, (Continued)

upon deployment, a user determines the prosthetic heart valve is not positioned optimally.

15 Claims, 19 Drawing Sheets

Related U.S. Application Data

(60) Provisional application No. 61/970,443, filed on Mar. 26, 2014.

(52) U.S. Cl.
CPC .... *A61F 2/2445* (2013.01); *A61F 2220/0008* (2013.01); *A61F 2220/0016* (2013.01); *A61F 2230/0065* (2013.01); *A61F 2230/0069* (2013.01)

(58) Field of Classification Search
CPC ...... A61F 2220/0008; A61F 2220/0016; A61F 2250/0039; A61F 2/2427; A61F 2/2442; A61F 2/82; A61F 2/90; A61F 2/848
See application file for complete search history.

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |

(56) References Cited

U.S. PATENT DOCUMENTS

| | | |
|---|---|---|
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,663 B2 | 9/2014 | Salahieh et al. |
| 8,870,948 B1* | 10/2014 | Erzberger ............ A61F 2/2439 623/2.1 |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 9,289,291 B2* | 3/2016 | Gorman, III ........ A61F 2/2409 |
| 9,439,757 B2* | 9/2016 | Wallace ............... A61F 2/2409 |
| 9,662,203 B2* | 5/2017 | Sheahan ............... A61F 2/2418 |
| 10,327,895 B2* | 6/2019 | Lozonschi ........... A61F 2/2469 |
| 10,583,002 B2* | 3/2020 | Lane .................... A61F 2/2436 |
| 10,729,541 B2* | 8/2020 | Francis ................ A61F 2/2412 |
| 10,856,975 B2* | 12/2020 | Hariton ................ B23P 15/001 |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0216310 A1 | 8/2009 | Straubinger et al. |
| 2009/0276027 A1 | 11/2009 | Glynn |
| 2009/0292350 A1 | 11/2009 | Eberhardt et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0082094 A1 | 4/2010 | Quadri et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0262231 A1* | 10/2010 | Tuval .................... A61F 2/24 623/2.4 |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0166636 A1* | 7/2011 | Rowe ................... A61F 2/2427 623/1.11 |
| 2011/0172765 A1 | 7/2011 | Nguyen et al. |
| 2011/0208283 A1 | 8/2011 | Rust |
| 2011/0208290 A1 | 8/2011 | Straubinger et al. |
| 2011/0264206 A1 | 10/2011 | Tabor |
| 2012/0022640 A1* | 1/2012 | Gross ................... A61F 2/2439 623/2.11 |
| 2012/0035722 A1 | 2/2012 | Tuval |
| 2012/0078347 A1 | 3/2012 | Braido et al. |
| 2012/0078353 A1 | 3/2012 | Quadri et al. |
| 2012/0101572 A1 | 4/2012 | Kovalsky et al. |
| 2012/0123529 A1 | 5/2012 | Levi et al. |
| 2012/0271398 A1 | 10/2012 | Essinger et al. |
| 2012/0303116 A1 | 11/2012 | Gorman, III et al. |
| 2012/0323317 A1* | 12/2012 | Karapetian .......... A61F 2/2409 623/2.37 |
| 2013/0030351 A1* | 1/2013 | Belhe .................. A61F 5/0076 604/9 |
| 2013/0190861 A1* | 7/2013 | Chau ................... A61F 2/2418 623/2.18 |
| 2013/0274873 A1 | 10/2013 | Delaloye et al. |
| 2013/0325114 A1* | 12/2013 | McLean ............... A61F 2/2409 623/2.12 |
| 2014/0018906 A1* | 1/2014 | Rafiee ................. A61F 2/2475 623/1.26 |
| 2014/0018915 A1 | 1/2014 | Biadillah et al. |
| 2014/0121763 A1 | 5/2014 | Duffy et al. |

(56) References Cited

U.S. PATENT DOCUMENTS

| | | |
|---|---|---|
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0277411 A1 | 9/2014 | Bortlein et al. |
| 2014/0277412 A1* | 9/2014 | Bortlein .............. A61F 2/2418 623/2.11 |
| 2014/0303719 A1 | 10/2014 | Cox et al. |
| 2014/0309727 A1* | 10/2014 | Lamelas ............ A61F 2/2466 623/2.11 |
| 2014/0324164 A1 | 10/2014 | Gross et al. |
| 2014/0343669 A1 | 11/2014 | Lane et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |
| 2014/0371844 A1* | 12/2014 | Dale .................. A61F 2/2418 623/2.11 |
| 2015/0025623 A1* | 1/2015 | Granada ............ A61F 2/2412 623/2.11 |
| 2015/0045881 A1* | 2/2015 | Lim .................. A61F 2/2418 623/2.38 |
| 2015/0142094 A1* | 5/2015 | Kassab .............. A61F 2/86 623/1.11 |
| 2015/0142103 A1* | 5/2015 | Vidlund ............ A61F 2/2439 623/2.17 |
| 2015/0216661 A1* | 8/2015 | Hacohen ........... A61B 17/0401 623/2.37 |
| 2015/0272730 A1* | 10/2015 | Melnick ............ A61F 2/2433 623/2.11 |
| 2016/0228248 A1* | 8/2016 | Rowe ................ A61F 2/2436 |
| 2016/0235529 A1* | 8/2016 | Ma .................... A61F 2/2412 |
| 2016/0278923 A1* | 9/2016 | Krans ................ A61F 2/2409 |
| 2016/0374801 A1* | 12/2016 | Jimenez ............ A61F 2/2418 623/2.18 |
| 2017/0056176 A1* | 3/2017 | Rowe ................ A61F 2/2454 |
| 2017/0258589 A1* | 9/2017 | Pham ................ A61F 2/2418 |
| 2018/0125633 A1* | 5/2018 | Fikfak .............. A61F 2/91 |
| 2018/0250126 A1* | 9/2018 | O'Connor ......... A61F 2/2409 |
| 2018/0296341 A1* | 10/2018 | Noe .................. A61F 2/2412 |
| 2018/0344457 A1* | 12/2018 | Gross ................ A61F 2/2418 |
| 2018/0353295 A1* | 12/2018 | Cooper ............. A61F 2/2418 |
| 2019/0038452 A1* | 2/2019 | Aravalli ............ A61F 5/445 |
| 2019/0060068 A1* | 2/2019 | Cope ................ A61F 2/2439 |
| 2019/0060070 A1* | 2/2019 | Groothuis .......... A61F 2/2466 |
| 2019/0167423 A1* | 6/2019 | Hariton ............. A61F 2/2418 |
| 2019/0175339 A1* | 6/2019 | Vidlund ............ A61F 2/2418 |
| 2019/0298559 A1* | 10/2019 | Gupta .............. A61B 1/2733 |
| 2020/0155307 A1* | 5/2020 | Quijano ............ A61F 2/2445 |
| 2020/0246140 A1* | 8/2020 | Hariton ............. A61F 2/2418 |
| 2020/0268512 A1* | 8/2020 | Mohl ................ A61F 2/2427 |
| 2020/0391016 A1* | 12/2020 | Passman ........... A61M 27/002 |
| 2021/0121290 A1* | 4/2021 | Alkhatib ........... A61F 2/2412 |
| 2021/0244557 A1* | 8/2021 | Belhe ................ A61F 5/0079 |
| 2021/0298896 A1* | 9/2021 | Pham ................ A61F 2/2409 |

FOREIGN PATENT DOCUMENTS

| | | |
|---|---|---|
| DE | 10121210 A1 | 11/2002 |
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| EP | 2537487 A1 | 12/2012 |
| FR | 2850008 A1 | 7/2004 |
| FR | 2847800 B1 | 10/2005 |
| JP | 2010523234 A | 7/2010 |
| JP | 2012504031 A | 2/2012 |
| JP | 2013521884 A | 6/2013 |
| JP | 2013540467 A | 11/2013 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03003943 A2 | 1/2003 |
| WO | 03047468 A1 | 6/2003 |
| WO | 06073626 A2 | 7/2006 |
| WO | 07071436 A2 | 6/2007 |
| WO | 08070797 A2 | 6/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2012127309 A1 | 9/2012 |

OTHER PUBLICATIONS

Andersen, H.R. et al, "Transluminal implantation of artificial heart valves," European Heart Journal, May 1992, pp. 704-708, vol. 13, No. 5.

Andersen, H.R., "Transluminal Catheter Implanted Prosthetic Heart Valves," International Journal of Angiology, Mar. 1998, pp. 102-106, vol. 7, No. 2.

Braido et al., U.S. Appl. No. 29/375,243, filed Sep. 20, 2010, titled "Surgical Stent Assembly".

Braido, Peter Nicholas, U.S. Appl. No. 29/375,260, filed Sep. 20, 2010, titled "Forked Ends".

Buellesfeld, et al., "Treatment of paravalvular leaks through inverventional techniques," Multimed Man Cardiothorac Surg., Department of Cardiology, Ben University Hospital, pp. 1-8, Jan. 2011.

De Cicco, et al., "Aortic valve periprosthetic leakage: anatomic observations and surgical results," The Annals of thoracic surgery, vol. 79, No. 5, pp. 1480-1485, May 2005.

Gössl,et al., "Percutaneous treatment of aortic and mitral valve paravalvular regurgitation," Current Cardiology Reports, vol. 15, No. 8., pp. 1-8, Aug. 2013.

Hourihan, et al., "Transcatheter Umbrella Closure of Valvular and Paravalvular Leaks," Journal of the American College of Cardiology, vol. 20, No. 6, pp. 1371-1377, Nov. 1992.

International Search Report and Written Opinion for Application No. PCT/US2015/021367 dated Jun. 25, 2015.

Knudsen, L.L. et al., "Catheter-implanted prosthetic heart valves," The International Journal of Artificial Organs, May 1993, pp. 253-262, vol. 16, No. 5.

Moazami, N. et al., Transluminal Aortic Valve Placement, ASAIO Journal, Sep.-Oct. 1996; pp. M381-M385, vol. 42, No. 5.

Muñoz, et al., "Guidance of treatment of perivalvular prosthetic leaks.", Current cardiology reports, 16.430, 6 pages, Jan. 2014.

Quaden, R. et al., "Percutaneous aortic valve replacement: resection before implantation," European J. of Cardio-thoracic Surgery, May 2005, pp. 836-840, vol. 27, No. 5.

Rohde, I., Masch, J.-M., Theisen-Kunde, D., Marczynski-Bühlow, M., Bombien Quaden, R., Lutter, G. and Brinkmann, R. (2015), Resection of Calcified Aortic Heart Leaflets In Vitro by Q-Switched 2 μm Microsecond Laser Radiation. Journal of Cardiac Surgery, 30: 157-162. doi:10.1111/jocs.12481.

Ruiz, C., "Overview of PRE-CE Mark Transcatheter Aortic Valve Technologies," Euro PCR, May 2010 (Powerpoint dated May 25, 2010).

Swiatkiewicz, et al., "Percutaneous closure of mitral perivalvular leak," Kardiologia Polska, vol. 67, No. 7, pp. 762-764, Jul. 2009.

Technology Frontier, "Heart repairs without surgery. Minimally invasive procedures aim to correct valve leakage", Heart Advisor/Sep. 2004, PubMed ID 15586429.

(56) References Cited

OTHER PUBLICATIONS

Zegdi, R., Md, PhD et al., "Is It Reasonable to Treat All Calcified Stenotic Aortic Valves With a Valved Stent?" J. of the American College of Cardiology, Feb. 5, 2008, pp. 579-584, vol. 51, No. 5.

* cited by examiner

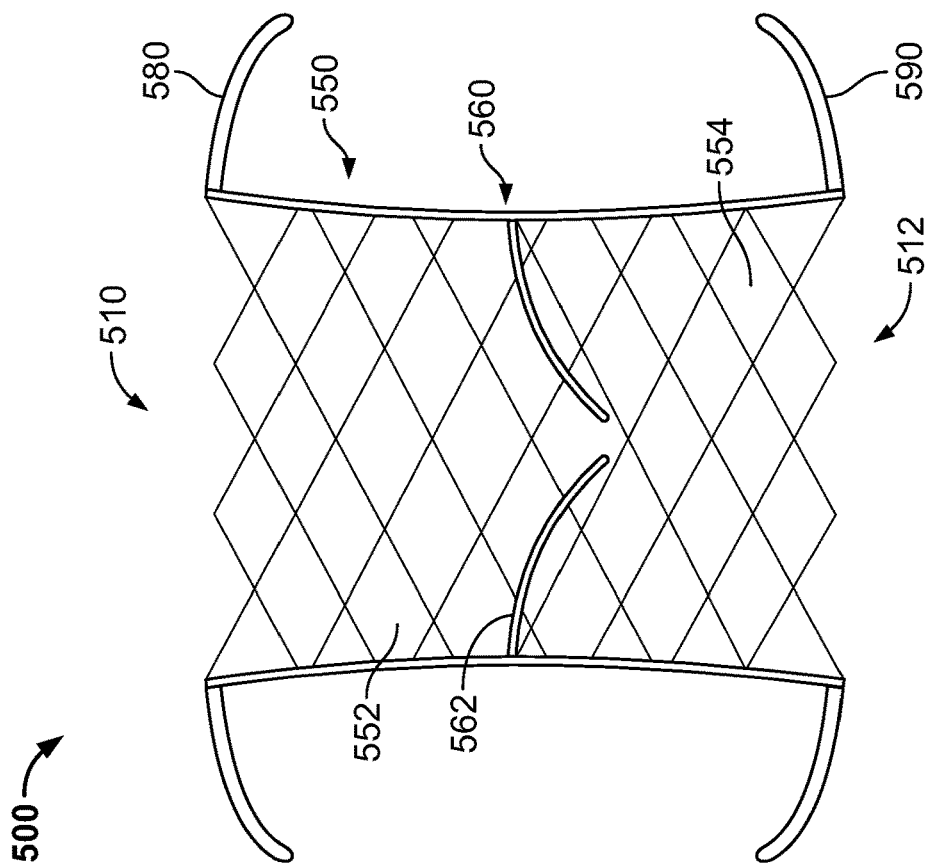
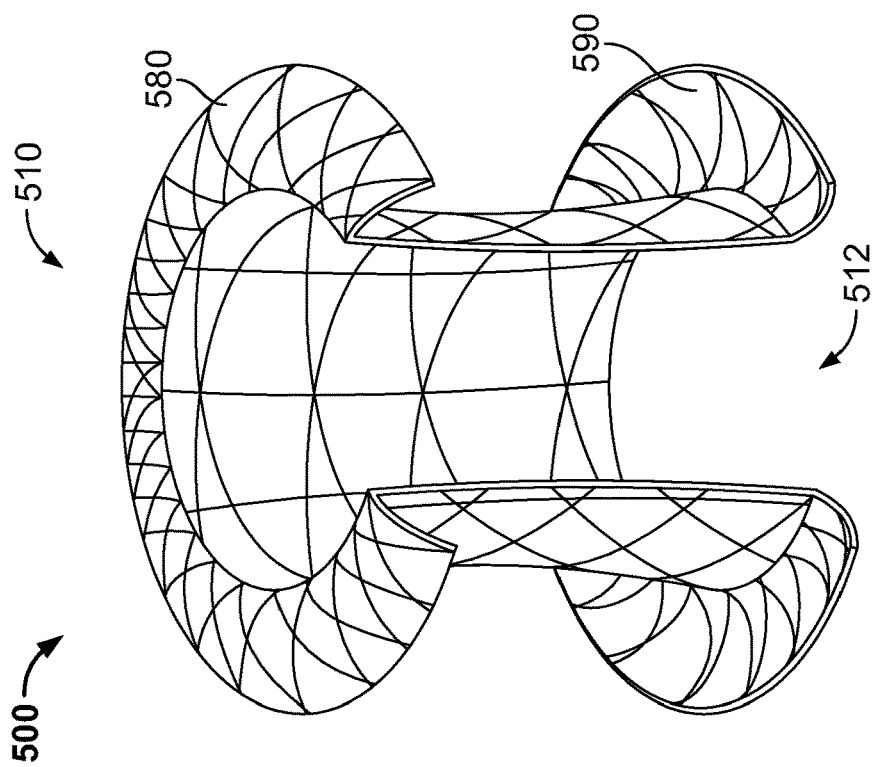

TRANSCATHETER MITRAL VALVE STENT FRAMES

CROSS-REFERENCE TO RELATED APPLICATIONS

The present application is a divisional of U.S. patent application Ser. No. 14/662,464, filed Mar. 19, 2015, which claims the benefit of the filing date of U.S. Provisional Patent Application No. 61/970,443 filed Mar. 26, 2014, the disclosures of which are both hereby incorporated herein by reference.

BACKGROUND

The present disclosure relates to heart valve replacement and, in particular, to collapsible prosthetic heart valves. More particularly, the present disclosure relates to designs for stent frames for collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve is generally first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY

According to one embodiment of the disclosure, a prosthetic heart valve may include a stent having an inflow end, an outflow end, a center portion between the inflow end and the outflow end, a collapsed condition, and an expanded condition. A collapsible and expandable valve assembly may be disposed within the stent and may have a plurality of leaflets. A first annular sealing member may be coupled to the inflow end and a second annular sealing member may be coupled to the outflow end.

According to another embodiment of the disclosure, a stent having an expanded condition and a collapsed condition may include a substantially cylindrical body having a first end and a second end. A flared portion may be coupled to the first end of the body and may extend radially outwardly from the body and away from the second end of the body when the stent is in the expanded condition. A plurality of anchor members may each have a first end coupled to the body and a second free end extending radially outwardly from the body and toward the first end of the body when the stent is in the expanded condition. The flared portion and the second free ends of the anchor members may be configured to extend away from the second end of the body when the stent is in the collapsed condition.

According to a further embodiment of the disclosure, a stent having an expanded condition and a collapsed condition may include a substantially cylindrical center body having a first end and a second end. A first plurality of anchor members may each have a first end coupled to the first end of the body and a second free end extending radially outwardly from the body and toward the second end of the body when the stent is in the expanded condition. A second plurality of anchor members may each have a first end coupled to the body and a second free end extending radially outwardly from the body and toward the second end of the body when the stent is in the expanded condition. The first and second plurality of anchor members may be configured to extend toward the second end of the body when the stent is in the collapsed condition.

According to still another embodiment of the disclosure, a stent having an expanded condition and a collapsed condition may include a substantially cylindrical center body having a first end and a second end. A first plurality of anchor members each having a first end coupled to the body and a second free end may extend radially outwardly from the body and toward the first end of the body when the stent is in the expanded condition. A second plurality of anchor members each having a first end coupled to the first end of the body and a second free end may extend radially outwardly from the body and toward the second end of the body when the stent is in the expanded condition. The first plurality of anchor members may extend toward the first end of the body and the second plurality of anchor members may extend toward the second end of the body when the stent is in the collapsed condition.

According to yet another embodiment of the disclosure, a stent having an expanded condition and a collapsed condition may include a substantially cylindrical center body having a first end, a second end, and a longitudinal axis extending between the first end and the second end. A first plurality of anchor members may each have a first end coupled to the body and a second free end extending radially outwardly from the body and substantially perpendicular to the longitudinal axis of the body when the stent is in the expanded condition. A second plurality of anchor members may each have a first end coupled to the body and a second free end extending radially outwardly from the body and substantially perpendicular to the longitudinal axis of the body when the stent is in the expanded condition. The first plurality of anchor members may extend away from the second end of the body and the second plurality of anchor members may extend away from the first end of the body when the stent is in the collapsed condition.

According to yet a further embodiment of the disclosure, a prosthetic heart valve may include a stent having an inflow end, an outflow end, a collapsed condition, and an expanded condition. The stent may be formed from wire and may have a first series of hooks and a second series hooks. A cuff may be coupled to the stent. When the stent is in the expanded condition, each hook of the first series may extend radially outwardly from the stent at the inflow end and each hook of the second series may include a first portion that extends radially outwardly from the stent at the outflow end and a second portion that extends toward the inflow end.

According to an even further embodiment of the disclosure, a prosthetic heart valve may include a stent having an inflow end, an outflow end, a collapsed condition, and an expanded condition. The stent may be formed of a plurality of struts. A collapsible and expandable valve assembly may be disposed within the stent and may have a plurality of leaflets. A commissure attachment feature may be attached to at least one of the plurality of struts and may be positioned between the inflow end and the outflow end when the stent is in the expanded condition.

BRIEF DESCRIPTION OF THE DRAWINGS

Various embodiments of the present disclosure are described herein with reference to the drawings, wherein:

FIG. 5A is a schematic cut-away perspective view of another prosthetic heart valve according to the present disclosure;

FIG. 5B is a longitudinal cross-section of the prosthetic heart valve of FIG. 5A;

Various embodiments of the present disclosure will now be described with reference to the appended drawings. It is to be appreciated that these drawings depict only some embodiments of the disclosure and are therefore not to be considered limiting of its scope.

DETAILED DESCRIPTION

Blood flows through the mitral valve from the left atrium to the left ventricle. As used herein, the term "inflow end," when used in connection with a prosthetic mitral heart valve, refers to the end of the heart valve closest to the left atrium when the heart valve is implanted in a patient, whereas the term "outflow end," when used in connection with a prosthetic mitral heart valve, refers to the end of the heart valve closest to the left ventricle when the heart valve is implanted in a patient. Further, when used herein with reference to a delivery device, the terms "proximal" and "distal" are to be taken as relative to a user using the device in an intended manner. "Proximal" is to be understood as relatively close to the user and "distal" is to be understood as relatively farther away from the user. Also, as used herein, the terms "substantially," "generally," and "about" are intended to mean that slight deviations from absolute are included within the scope of the term so modified. Generally, materials described as being suitable for components in one embodiment may also be suitable for similar components described in other embodiments.

Figure 1:
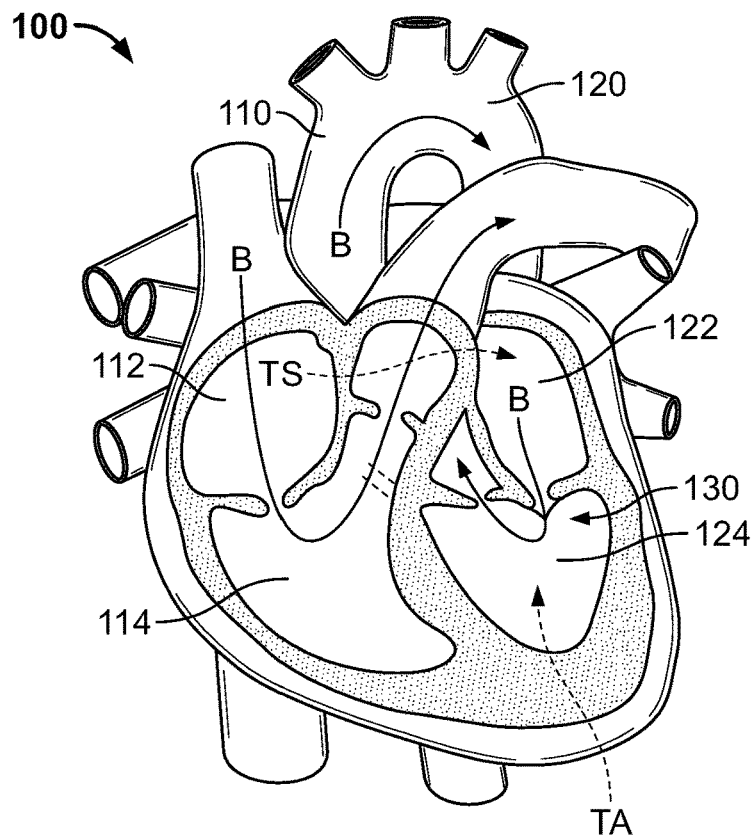
FIG. 1 is a schematic cutaway representation of a human heart showing a transapical delivery approach.

FIG. 1 is a schematic cutaway representation of human heart 100. The human heart includes two atria and two ventricles: right atrium 112 and left atrium 122, and right ventricle 114 and left ventricle 124. Heart 100 further includes aorta 110, and aortic arch 120. Disposed between the left atrium and the left ventricle is mitral valve 130. Mitral valve 130, also known as the bicuspid valve or left atrioventricular valve, is a dual-flap that opens as a result of increased pressure in left atrium 122 as it fills with blood. As atrial pressure increases above that of left ventricle 124, mitral valve 130 opens and blood passes into left ventricle 124. Blood flows through heart 100 in the direction shown by arrows "B".

A dashed arrow, labeled "TA", indicates a transapical approach of implanting a prosthetic heart valve, in this case to replace the mitral valve. In transapical delivery, a small incision is made between the ribs and into the apex of left ventricle 124 to deliver the prosthetic heart valve to the target site. A second dashed arrow, labeled "TS", indicates a transseptal approach of implanting a prosthetic heart valve in which the valve is passed through the septum between right atrium 112 and left atrium 122. Other approaches for implanting a prosthetic heart valve are also possible.

Figure 2:
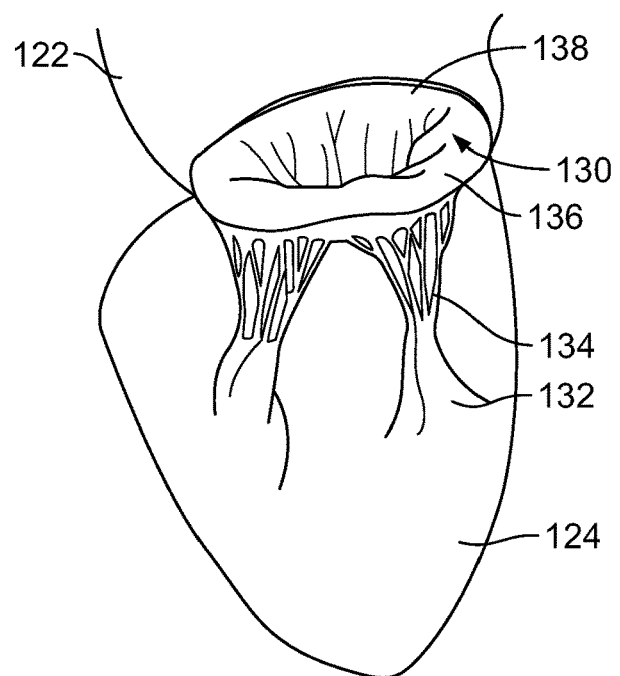
FIG. 2 is a schematic representation of a native mitral valve and associated cardiac structures.

FIG. 2 is a more detailed schematic representation of native mitral valve 130 and its associated structures. As previously noted, mitral valve 130 includes two flaps or leaflets, posterior leaflet 136 and anterior leaflet 138, disposed between left atrium 122 and left ventricle 124. Cord-like tendons, known as chordae tendineae 134, connect the two leaflets 136, 138 to the medial and lateral papillary muscles 132. During atrial systole, blood flows from higher pressure in left atrium 122 to lower pressure in left ventricle 124. When left ventricle 124 contracts in ventricular systole, the increased blood pressure in the chamber pushes leaflets 136, 138 to close, preventing the backflow of blood into left atrium 122. Since the blood pressure in left atrium 122 is much lower than that in left ventricle 124, leaflets 136, 138 attempt to evert to the low pressure regions. Chordae tendineae 134 prevent the eversion by becoming tense, thus pulling on leaflets 136, 138 and holding them in the closed position.

Figure 3B:
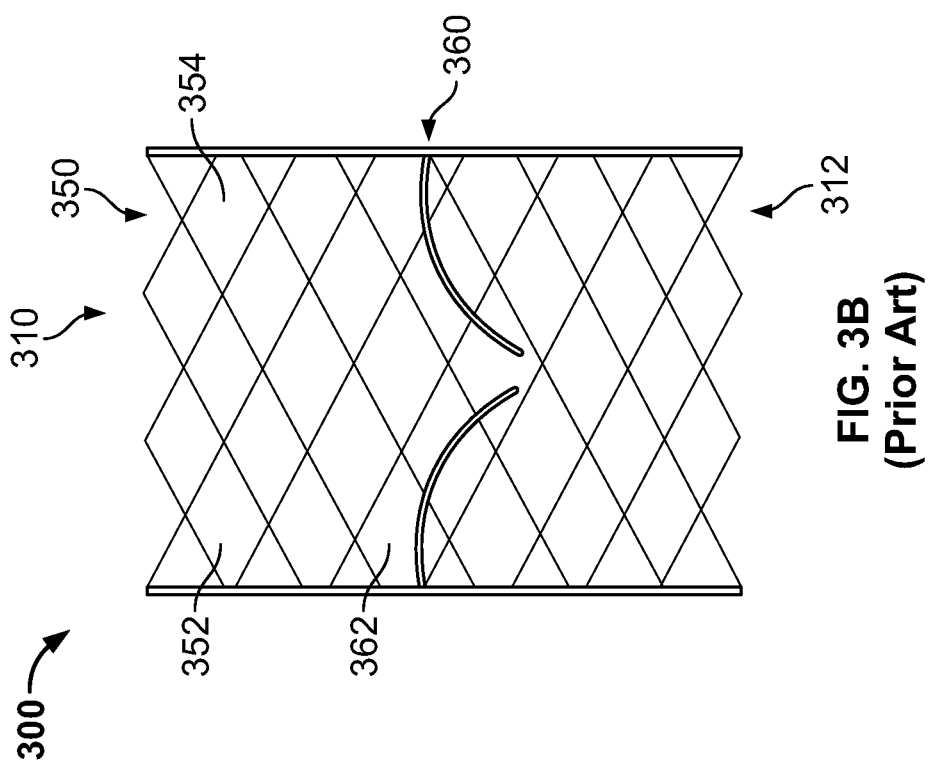
FIG. 3B is a longitudinal cross-section of the prosthetic heart valve of FIG. 3A.
Figure 3A:
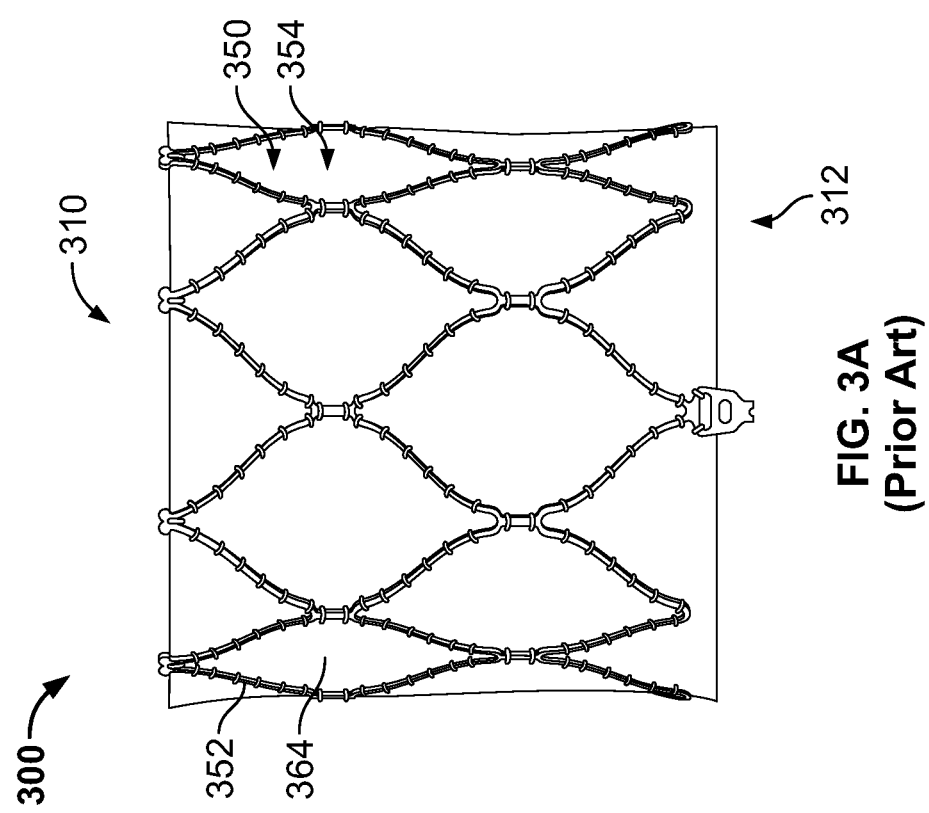
FIG. 3A is a side view of a prosthetic heart valve according to the prior art.

FIGS. 3A and 3B are a side view and a longitudinal cross-sectional view of prosthetic heart valve 300 according to the prior art. Prosthetic heart valve 300 is a collapsible prosthetic heart valve designed to replace the function of the native mitral valve of a patient (see native mitral valve 130 of FIGS. 1-2). Generally, prosthetic valve 300 has a substantially cylindrical shape with inflow end 310 and outflow end 312. When used to replace native mitral valve 130, prosthetic valve 300 may have a low profile so as not to interfere with atrial function in the native valve annulus.

Prosthetic heart valve 300 may include stent 350, which may be formed from biocompatible materials that are capable of self-expansion, such as, for example, shape memory alloys including Nitinol. Stent 350 may include a plurality of struts 352 that form cells 354 connected to one another in one or more annular rows around the stent. Cells 354 may all be of substantially the same size around the perimeter and along the length of stent 350. Alternatively, cells 354 near inflow end 310 may be larger than the cells near outflow end 312. Stent 350 may be expandable to provide a radial force to assist with positioning and stabilizing prosthetic heart valve 300 in the native valve annulus.

Prosthetic heart valve 300 may also include a substantially cylindrical valve assembly 360 including a pair of leaflets 362 (FIG. 3B) attached to a cuff 364 (FIG. 3A). Leaflets 362 replace the function of native mitral valve leaflets 136 and 138 described above with reference to FIG. 2. That is, leaflets 362 coapt with one another to function as a one-way valve. Though prosthetic heart valve 300 is illustrated as having a valve assembly 360 with two leaflets 362, it will be appreciated that prosthetic heart valve 300 may have more than two leaflets when used to replace the mitral valve or other cardiac valves within a patient. Both cuff 364 and leaflets 362 may be wholly or partly formed of any suitable biological material, such as bovine or porcine pericardium, or polymers, such as polytetrafluoroethylene (PTFE), urethanes and the like. Valve assembly 360 may be secured to stent 350 by suturing to struts 352 or by using tissue glue, ultrasonic welding or other suitable methods.

When prosthetic heart valve 300 is implanted in a patient, for example at the annulus of native mitral valve 130, it is biased towards an expanded condition, providing radial force to anchor the valve in place. However, if the radial force is too high, damage may occur to heart tissue. If, instead, the radial force is too low, the heart valve may move from its implanted position, for example, into either left ventricle 124 or left atrium 122, requiring emergency surgery to remove the displaced valve. The potential for such movement may be heightened in mitral valve applications, particularly if a low profile valve is used.

Another potential issue with prosthetic heart valves is inadequate sealing between the prosthetic valve and the native tissue. For example, if prosthetic heart valve 300 is implanted at the annulus of mitral valve 130 in a patient, improper or inadequate sealing may result in blood flowing from left ventricle 124 into left atrium 122, even if leaflets 362 of valve assembly 360 are working properly. This may occur, for example, if blood flows in a retrograde fashion between the outer perimeter of prosthetic heart valve 300 and the native tissue at the site of implantation. This phenomenon is known as perivalvular (or paravalvular) leak ("PV leak").

Figure 4B:
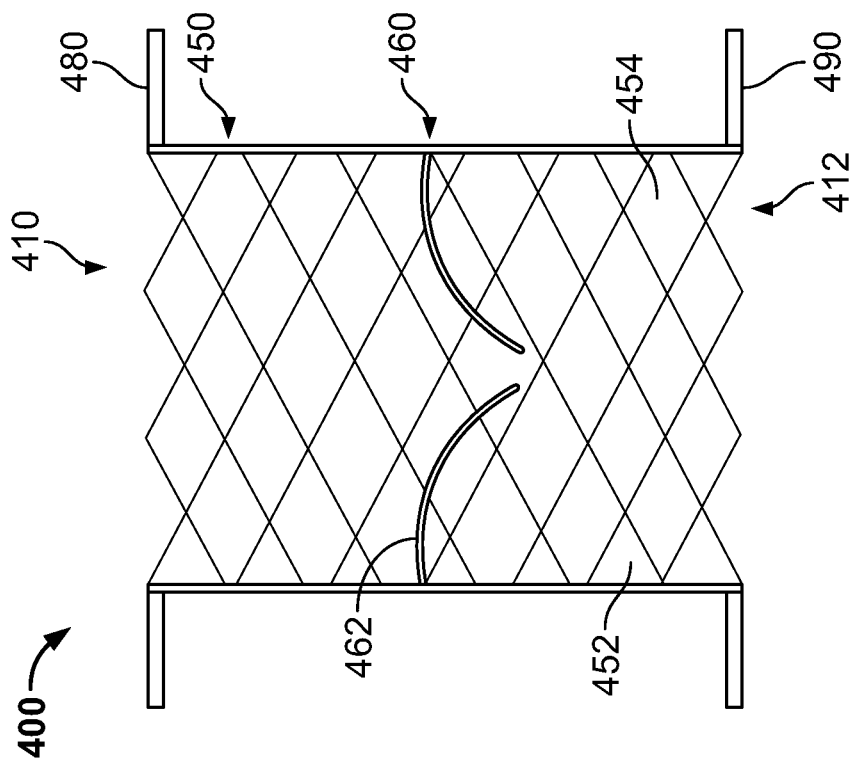
FIG. 4B is a longitudinal cross-section of the prosthetic heart valve of FIG. 4A.
Figure 4A:
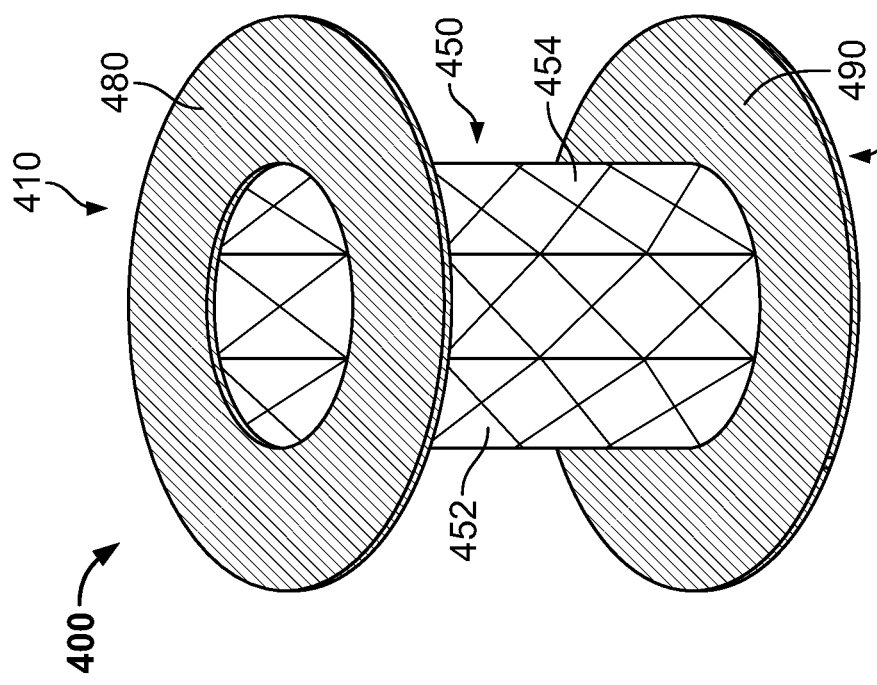
FIG. 4A is a schematic perspective view of a prosthetic heart valve according to the present disclosure.

FIGS. 4A and 4B illustrate a prosthetic heart valve 400 according to one embodiment of the disclosure in perspective and longitudinal cross-section views, respectively. Prosthetic heart valve 400 is a collapsible prosthetic heart valve designed to replace the function of the native mitral valve of a patient. Generally, prosthetic valve 400 has inflow end 410 and outflow end 412.

Prosthetic heart valve 400 may include stent 450, which may be formed from biocompatible materials that are capable of self-expansion, such as, for example, shape memory alloys including Nitinol. Stent 450 may include a plurality of struts 452 that form cells 454 connected to one another in one or more annular rows around the stent. Stent 450 may be radially expandable to provide a radial force to assist with positioning and stabilizing prosthetic heart valve 400 in the native mitral valve annulus. Stent 450 may be substantially cylindrically shaped when in the expanded condition.

Prosthetic heart valve 400 may also include valve assembly 460 including a pair of leaflets 462. Leaflets 462 function similarly to leaflets 362 described above in connection with FIG. 3B, and more or fewer leaflets may be used in other applications.

A number of sealing elements may be provided on prosthetic heart valve 400. In particular, prosthetic heart valve 400 may include a first sealing ring 480 positioned at inflow end 410 and a second sealing ring 490 positioned at outflow end 412. Each sealing ring 480, 490 may be formed of a biocompatible material that allows tissue ingrowth. For example, sealing rings 480 and 490 may be formed of fabrics and/or polymers, such as polytetrafluoroethylene (PTFE), urethanes and the like. Alternatively, sealing rings 480 and 490 may be formed of traditional stent materials, such as shape memory alloys including Nitinol, and may take forms including Nitinol coils. In still other embodiments, sealing rings 480 and 490 may be formed from a metal or polymer mesh or braid. Still further, sealing rings 480, 490 may be formed of tissue, such as porcine cardiac tissue. Some or all of the above materials may be used in combination with a coating, such as a collagen coating, a fibrin coating, or a polymer coating (such as a silicone coating). Sealing rings 480 and 490 may be attached to inflow end 410 and outflow end 412, respectively, by, for example, sutures, adhesives, ultrasonic welding or other suitable methods. Alternatively, if sealing rings 480 and 490 are formed of the same material as stent 450, sealing rings 480 and 490 may be formed integrally with stent 450.

Figure 4C:
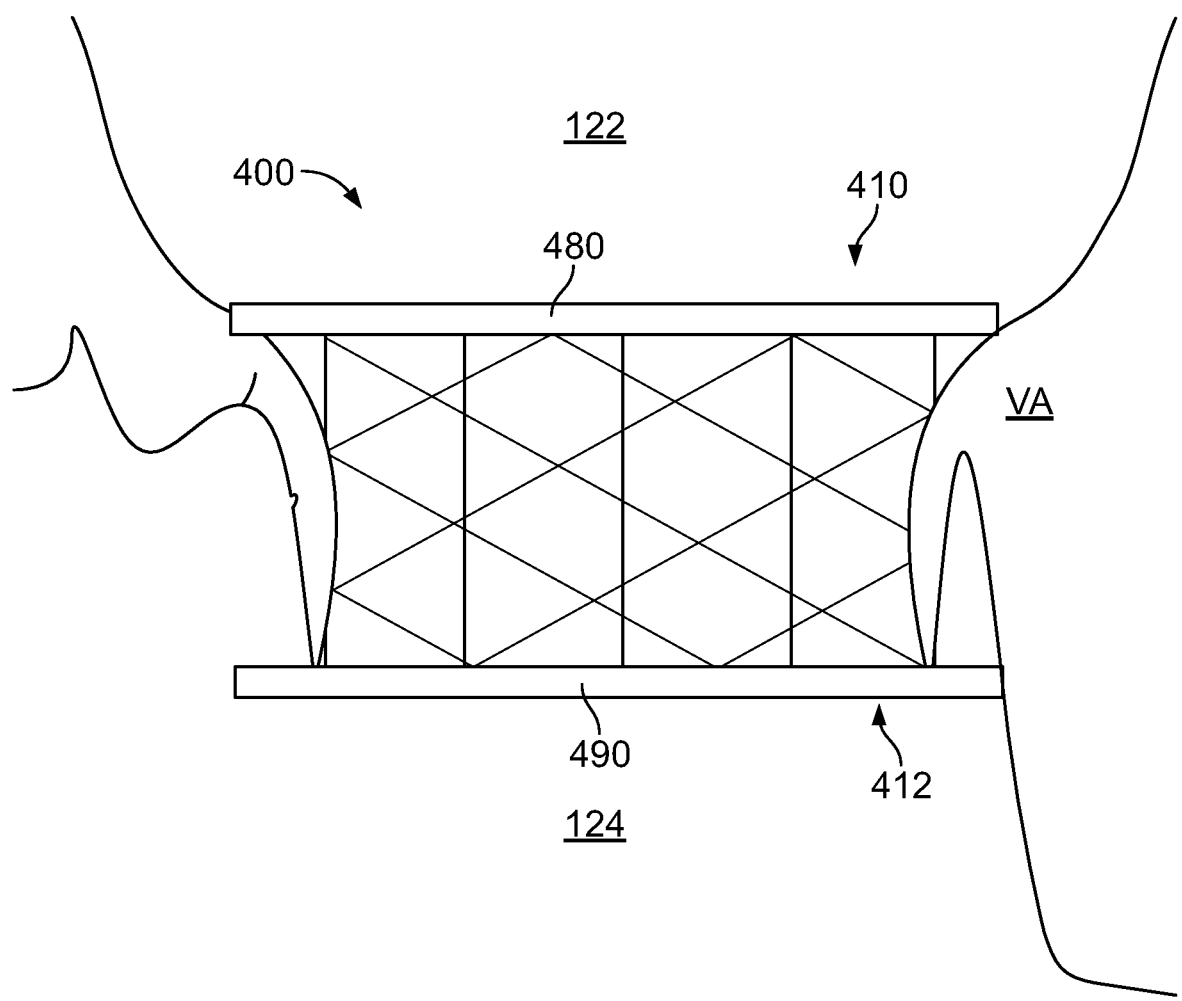
FIG. 4C is a schematic representation of the prosthetic heart valve of FIG. 4A disposed in a native valve annulus.

Each sealing ring 480, 490 is generally annular, with a center portion of each sealing ring being attached to stent 450 so that blood may flow through the stent. Sealing rings 480 and 490 may each have an outer diameter that is greater than the diameter of stent 450 when in the expanded condition. When stent 450 is in the expanded condition, sealing rings 480 and 490 each have a substantially planar configuration. However, other shapes and sizes may be suitable depending on the particular anatomy of the patient. FIG. 4C shows prosthetic heart valve 400 implanted within native valve annulus VA between left atrium 122 and left ventricle 124. In the implanted position, first sealing ring 480 is positioned on the atrial side of native valve annulus VA while second sealing ring 490 is positioned on the ventricular side of native valve annulus VA. Sealing rings 480 and 490 may help prevent PV leak by preventing blood from flowing from left ventricle 124 to left atrium 122 between the native valve annulus VA and the outer perimeter of prosthetic heart valve 400. This function may be enhanced once tissue begins to grow into first sealing ring 480 and second sealing ring 490.

In addition to helping prevent PV leak, sealing ring 480 may provide an anchoring effect, helping to prevent prosthetic heart valve 400 from migrating toward left ventricle 124. Similarly, second sealing ring 490 may also provide an anchoring effect, helping to prevent prosthetic heart valve 400 from migrating toward left atrium 122. This additional anchoring ability may reduce the radial force required of stent 450 to keep prosthetic heart valve 400 secured in native valve annulus VA, which, in turn, may allow stent 450 to have a smaller fully expanded diameter than traditional stents. This reduction in size may be possible, in part, due to a reduction or elimination of the need to have a relatively large stent frame to maximize the range of anatomies which could accept the stent and still have enough radial force to hold the stent in place. The relatively smaller diameter which may be possible due to the above-described features may result in lower hydrodynamic load on prosthetic heart valve 400, which may reduce the stresses on valve assembly 460 and which also may reduce the strain on the material forming stent 450.

FIGS. 5A and 5B illustrate a prosthetic heart valve 500 according to another embodiment of the disclosure. Prosthetic heart valve 500 is similar to prosthetic heart valve 400 in certain respects. For example, prosthetic heart valve 500 may include stent 550, which may be formed from biocompatible materials that are capable of self-expansion, such as, for example, shape memory alloys including Nitinol. Stent 550 may include a plurality of struts 552 that form cells 554 connected to one another in one or more annular rows around the stent. Stent 550 may be radially expandable to provide a radial force to assist with positioning and stabilizing prosthetic heart valve 500 in the native valve annulus. Stent 550 has the general shape of a cylinder, except that it is bowed inwardly from inflow end 510 and outflow end 512 toward the center. In other words, stent 550 has a concave shape, wherein the center of stent 550 has a smaller diameter than that of inflow end 510 and outflow end 512 when in the expanded condition.

Prosthetic heart valve 500 may also include valve assembly 560 including a pair of leaflets 562. Leaflets 562 function similarly to leaflets 362 described above in connection with FIG. 3B, and more or fewer leaflets may be used in other applications.

Prosthetic heart valve 500 may also include a number of sealing elements. In particular, prosthetic heart valve 500 may include a first sealing ring 580 positioned at inflow end 510 and a second sealing ring 590 positioned at outflow end 512. Sealing rings 580, 590 may be generally similar to sealing rings 480, 490, with the exception that first sealing ring 580 is curved toward outflow end 512 and second sealing ring 590 is curved toward inflow end 510. In other words, sealing rings 580 and 590 are substantially non-planar when stent 550 is in the expanded condition. Sealing rings 580, 590 may be formed of the same biocompatible materials described above for forming sealing rings 480 and 490, and may be attached to inflow end 510 and outflow end 512, respectively, in the same manner as sealing rings 480 and 490.

Each sealing ring 580, 590 is generally annular, with a center portion of each sealing ring being attached to stent 550 so that blood may flow through the stent. As described above, sealing rings 580, 590 may be curved away from the ends of stent 550 to which the rings are attached. In other words, the outer perimeter of first sealing ring 580 is closer to outflow end 512 than the inner perimeter of that sealing ring. Similarly, the outer perimeter of second sealing ring 590 is closer to inflow end 510 than the inner perimeter of that sealing ring. However, other shapes and sizes may be suitable depending on the particular anatomy of the patient.

Figure 5C:
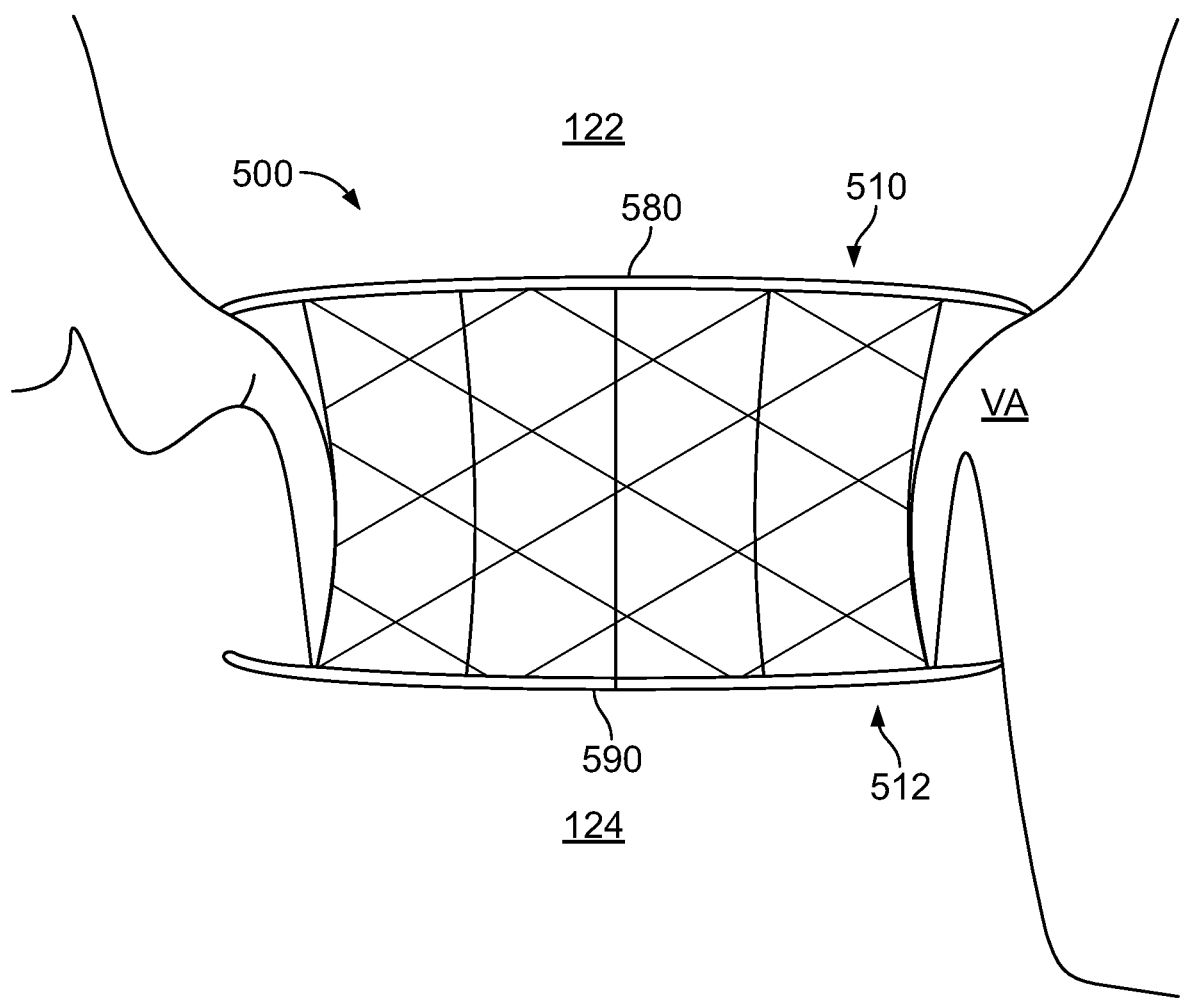
FIG. 5C is a schematic representation of the prosthetic heart valve of FIG. 5A disposed in a native valve annulus.

FIG. 5C shows prosthetic heart valve 500 implanted within native valve annulus VA between left atrium 122 and left ventricle 124. In the implanted position, first sealing ring 580 is positioned on the atrial side of native valve annulus VA while second sealing ring 590 is positioned on the ventricular side of native valve annulus VA. In these positions, sealing rings 580 and 590 mitigate PV leak by preventing blood from flowing from left ventricle 124 to left atrium 122 between the native valve annulus VA and the outer perimeter of prosthetic heart valve 500. Once tissue begins to grow into first sealing ring 580 and second sealing ring 590, PV leak may be mitigated to an even greater extent.

In addition to helping prevent PV leak, first sealing ring 580 may provide an anchoring effect, helping to prevent prosthetic heart valve 500 from migrating toward left ventricle 124. Similarly, second sealing ring 590 may also provide an anchoring effect, helping to prevent prosthetic heart valve 500 from migrating toward left atrium 122. The curvature of sealing rings 580 and 590 may dictate, in part, how prosthetic heart valve 500 interacts with the anatomy and how stresses are distributed in valve 500. The above-described curvature may have an enhanced effect on sealing and anchoring in comparison to a relatively flat or planar sealing ring. This may be due, in part, to the anatomy near the implant site having generally non-planar surfaces. Further, the curvature of sealing rings 580 and 590 may effectively pinch tissue of the annulus resulting in enhanced sealing and anchoring, while also increasing apposition to the annulus by forcing any irregular anatomic geometries into the pinched area. In addition, the inwardly bowed shape of stent 550 may provide a greater contact area between stent 550 and the native valve annulus VA.

Figure 6A:
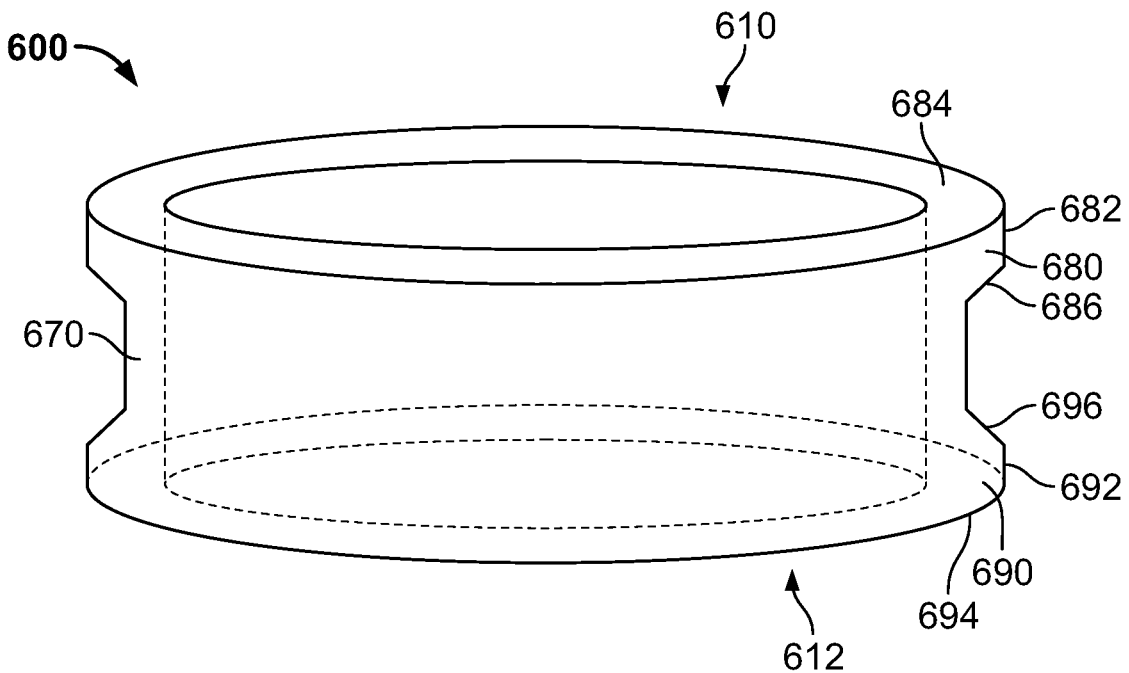
FIG. 6A is a schematic perspective view of a docking station for use with a prosthetic heart valve.
Figure 6B:
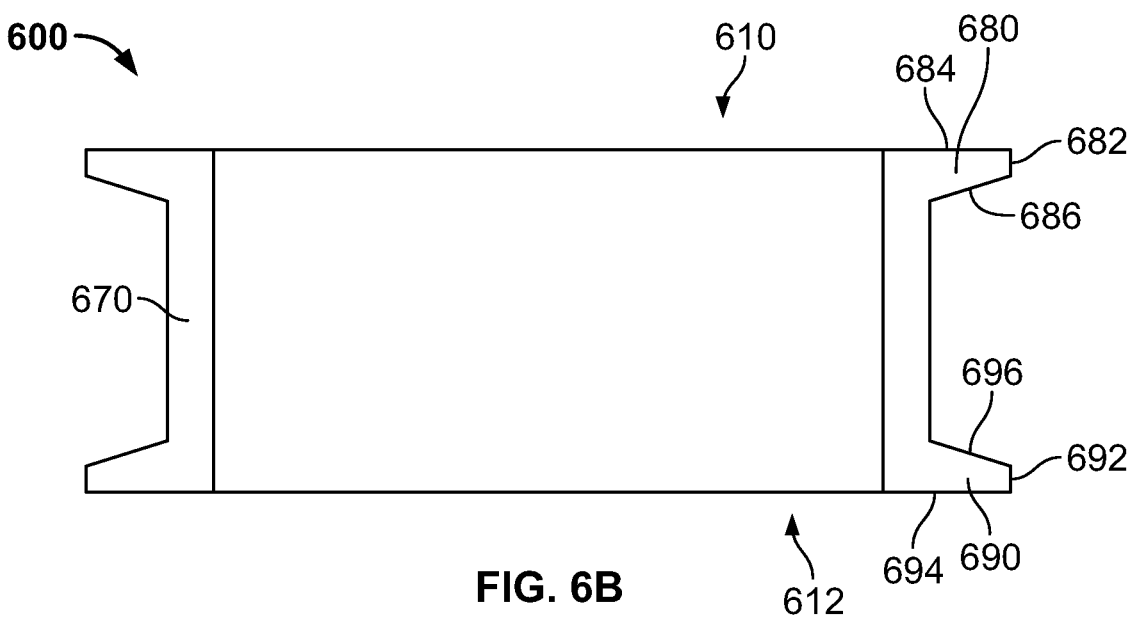
FIG. 6B is a cross-sectional view of the docking station of FIG. 6A.

FIGS. 6A and 6B illustrate a prosthetic heart valve docking station 600 according to one embodiment of the disclosure in perspective and longitudinal cross-sectional views, respectively. As is described below, docking station 600 may first be implanted in a native valve annulus, and a prosthetic heart valve may be subsequently implanted in docking station 600.

Docking station 600 has inflow end 610 and outflow end 612, and may be formed from biocompatible materials that are capable of self-expansion, such as, for example, shape memory alloys including Nitinol. Docking station 600 may alternatively be made of a material that is not self-expandable, such as stainless steel, which may be expanded with the use of a separate expandable structure, such as a balloon.

Docking station 600 may have the general form of a hollow tube with a cylindrical center section 670 and anchoring members extending radially outwardly at inflow end 610 and outflow end 612. For example, the illustrated embodiment of docking station 600 includes first anchor rim 680 and second anchor rim 690. The particular shape of each anchor rim 680, 690 may be varied. For example, first anchor rim 680 may have a cylindrical outer surface 682 that is substantially concentric to cylindrical center section 670. One end surface 684 of anchor rim 680 coextensive with inflow end 610 may lie in a plane perpendicular to the axis of rotation of central section 670. The other end surface 686 of anchor rim 680 may be inclined at an oblique angle to the axis of rotation of central section 670. Second anchor rim 690 may have a similar structure. That is, second anchor rim 690 may have a cylindrical outer surface 692 that is substantially concentric to center section 670. One end surface 694 of anchor rim 690 coextensive with outflow end 612 may lie in a plane perpendicular to the axis of rotation of center section 670, while the other end surface 696 of anchor rim 690 may be inclined at an oblique angle to that axis of rotation. The inclined surfaces of anchor rims 680 and 690 may provide better contact with a native valve annulus, but may be varied and still be within the scope of this disclosure.

Figure 6C:
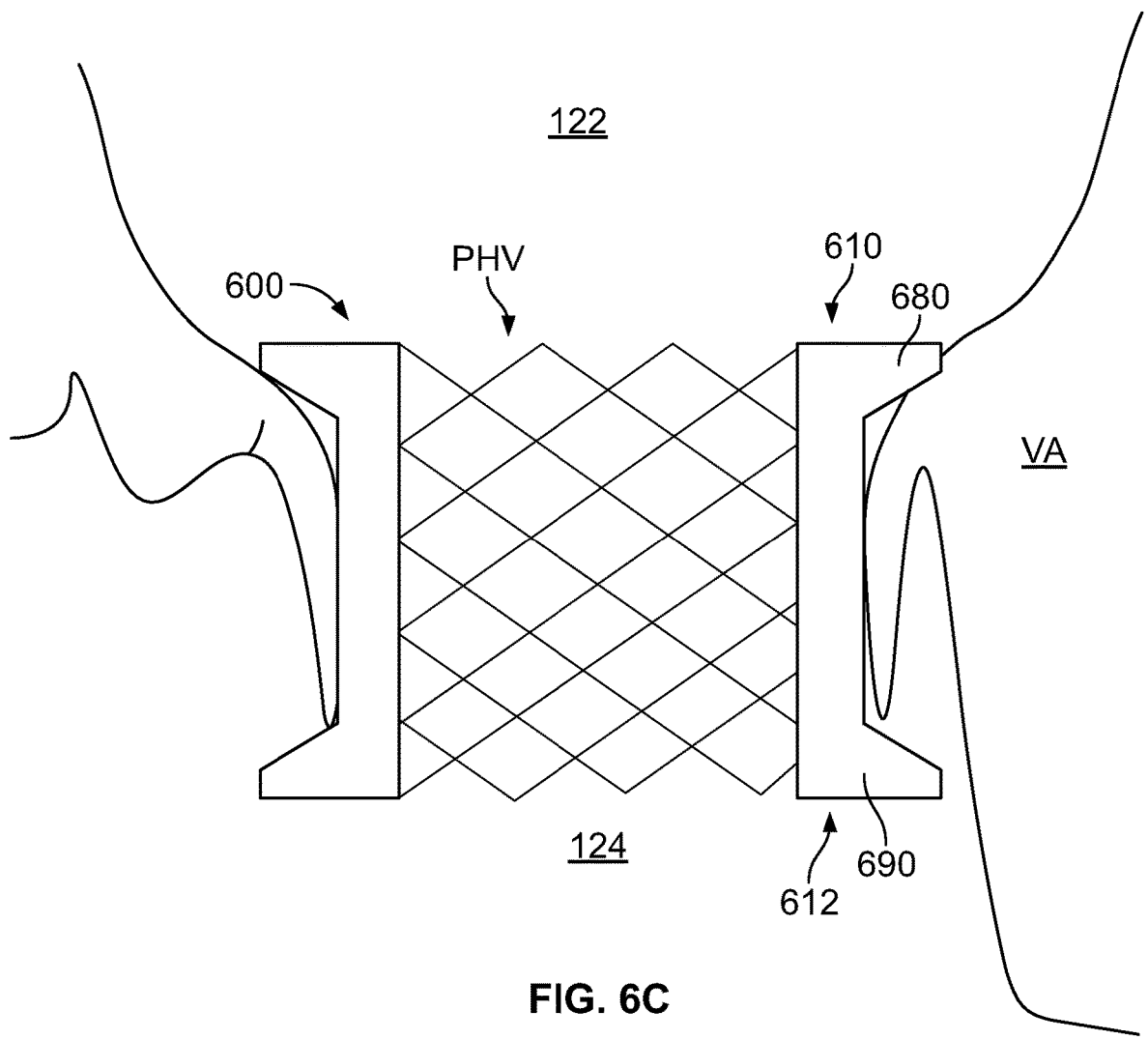
FIG. 6C is a schematic representation of the docking station of FIG. 6A disposed in a native valve annulus with a prosthetic heart valve disposed within the docking station.

FIG. 6C shows docking station 600 implanted within native valve annulus VA between left atrium 122 and left ventricle 124. In the implanted position, first anchor rim 680 is positioned on the atrial side of native valve annulus VA while anchor rim 690 is positioned on the ventricular side of native valve annulus VA. Anchor rims 680 and 690 may provide an anchoring effect, helping prevent docking station 600 from migrating toward left ventricle 124 or left atrium 122. Once docking station 600 has been implanted as described, prosthetic heart valve PHV may be assembled to the docking station.

A number of benefits may result from using a two-step process in which docking station 600 is first implanted within native valve annulus VA and then prosthetic heart valve PHV is assembled to docking station 600. For example, when implanted, prosthetic heart valve PHV, which may take the form of any traditional prosthetic heart valve or any of the embodiments disclosed herein, will encounter a predictable environment. That is, the variability in anatomy from one patient to another will have less effect on the positioning and functioning of prosthetic heart valve PHV, because prosthetic heart valve PHV will interact directly with docking station 600 rather than with the anatomy of native valve annulus VA.

Figure 7A:
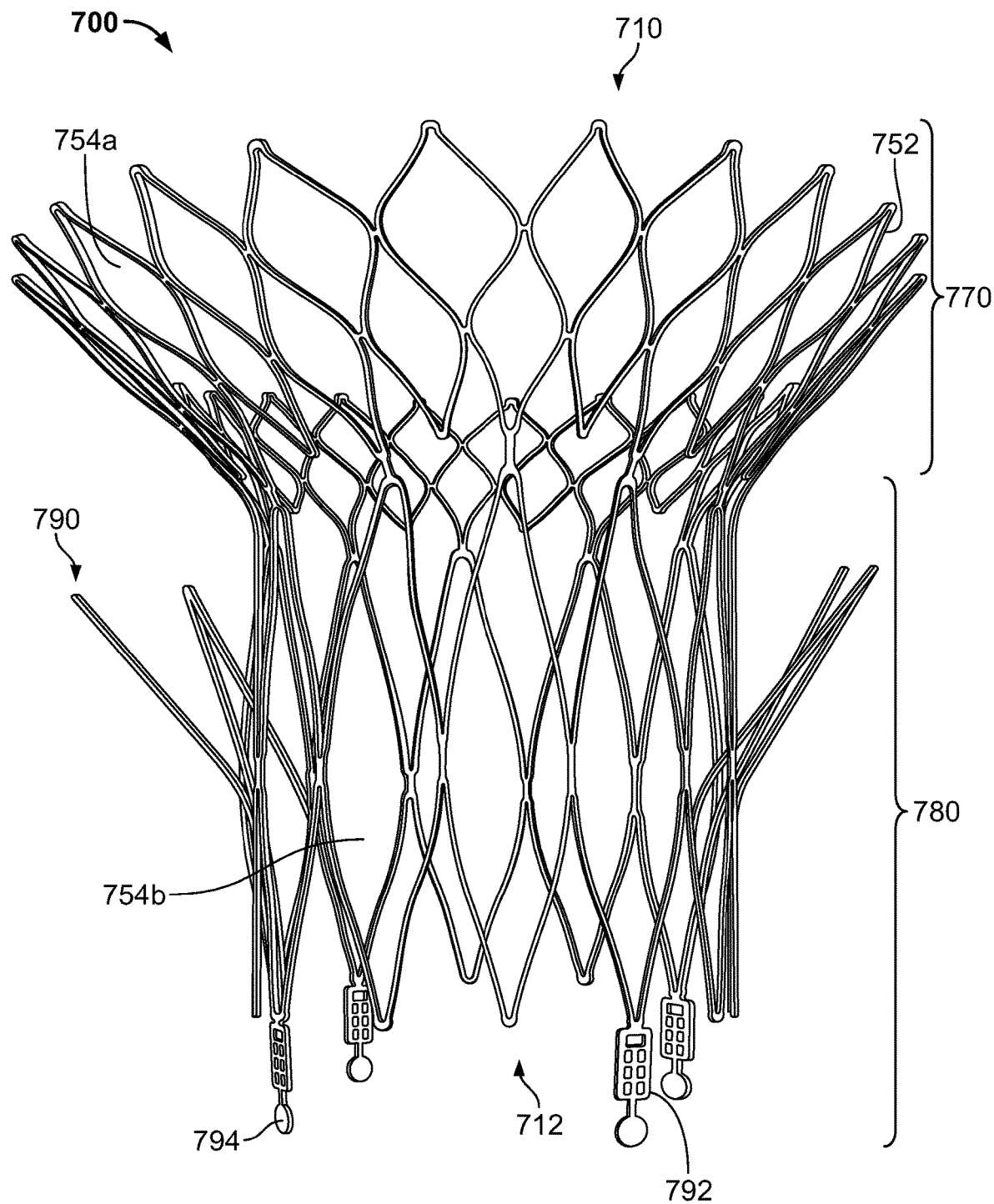
FIG. 7A is a perspective view of a stent of a prosthetic heart valve according to the present disclosure.

FIG. 7A illustrates a stent 700 of a prosthetic heart valve according to one embodiment of the disclosure. Stent 700 is collapsible and expandable for use in a prosthetic heart valve intended to replace the function of the native mitral valve of a patient. In FIG. 7A, stent 700 is illustrated in its expanded condition. The remaining components that would be attached to stent 700 to form a prosthetic heart valve, such as leaflets and a cuff, are omitted from the figures for clarity.

Stent 700 has inflow end 710 and outflow end 712, and may be formed from biocompatible materials that are capable of self-expansion, such as, for example, shape memory alloys including Nitinol. Stent 700 may include a plurality of struts 752 that form cells connected to one another in one or more annular rows around the stent.

Stent 700 may be thought of as having at least three main portions. At inflow end 710 is flared portion 770, which flares radially outwardly in a direction away from outflow end 712. Flared portion 770 may include one or more circumferential rows of relatively small cells 754*a*. Each cell 754*a* is formed from a group of struts 752 that defines a geometric shape having a relatively small area, in this case generally a diamond shape.

Stent 700 also includes a substantially cylindrical body 780 that extends from flared portion 770 to outflow end 712 of the stent. Body 780 may include one or more circumferential rows of relatively large cells 754*b*. Each cell 754*b* is formed from a group of struts 752 that defines a geometric shape having a relatively large area, in this case generally a diamond shape. Struts 752 forming larger cells 754*b* may be thicker and stronger than struts 752 forming smaller cells 754*a*. Rows of relatively small cells 754*a* may be thought of as being a high-density arrangement of cells, while rows of relatively large cells 754*b* may be thought as being a low-density arrangement of cells.

Stent 700 also includes a portion with anchor members, in this case hooks 790. Hooks 790 are formed of struts 752 that extend radially outwardly toward inflow end 710. Hooks 790 may be integral with stent 700, being formed from the same single piece of starting material, and may be connected to stent 700 anywhere on body 780. It should be noted that the term hooks may include other anchoring structures, for example barbs or clips.

When being used in a prosthetic heart valve for replacing the native mitral valve of a patient, stent 700 is crimped to a collapsed condition and positioned within a catheter or similar structure of a delivery device. The delivery device may, for example, be inserted through the apex of the heart (transapical delivery) or through the femoral artery and passed through the vasculature to the implant site (transfemoral delivery). Once the delivery device is near the site of implantation, the sheath or other member compressing stent 700 may be slowly retracted to reveal stent 700 and allow it to expand to the expanded condition. If a transapical method is used with a split sheath, as a proximal portion of the sheath is retracted proximally, hooks 790 are first released from the proximal portion of the sheath and expand. The release of hooks 790 may be performed in left ventricle 124 and then pushed distally until hooks 790 catch native leaflets 136 and 138. Alternately, the release of hooks 790 may be performed in left atrium 122, then pulled proximally into left ventricle 124 and then pushed back to catch native leaflets 136 and 138. The initial release of hooks 790 may be accomplished with other types of sheaths, for example with a double proximal sheath with a slot or other opening in the inner sheath to allow hooks 790 to deploy first. It should be noted that in the collapsed condition, hooks 790 point toward inflow end 710, rather than toward outflow end 712. In other words, hooks 790 (as well as flared portion 770) are folded toward left atrium 122 during deployment, such that hooks 790 may gradually expand outwardly as the delivery sheath is slowly retracted. If, on the other hand, hooks 790 were delivered folded toward left ventricle 124, once the delivery sheath cleared hooks 790, the hooks would suddenly flip nearly 180 degrees, possibly causing trauma to native valve annulus VA.

Figure 7B:
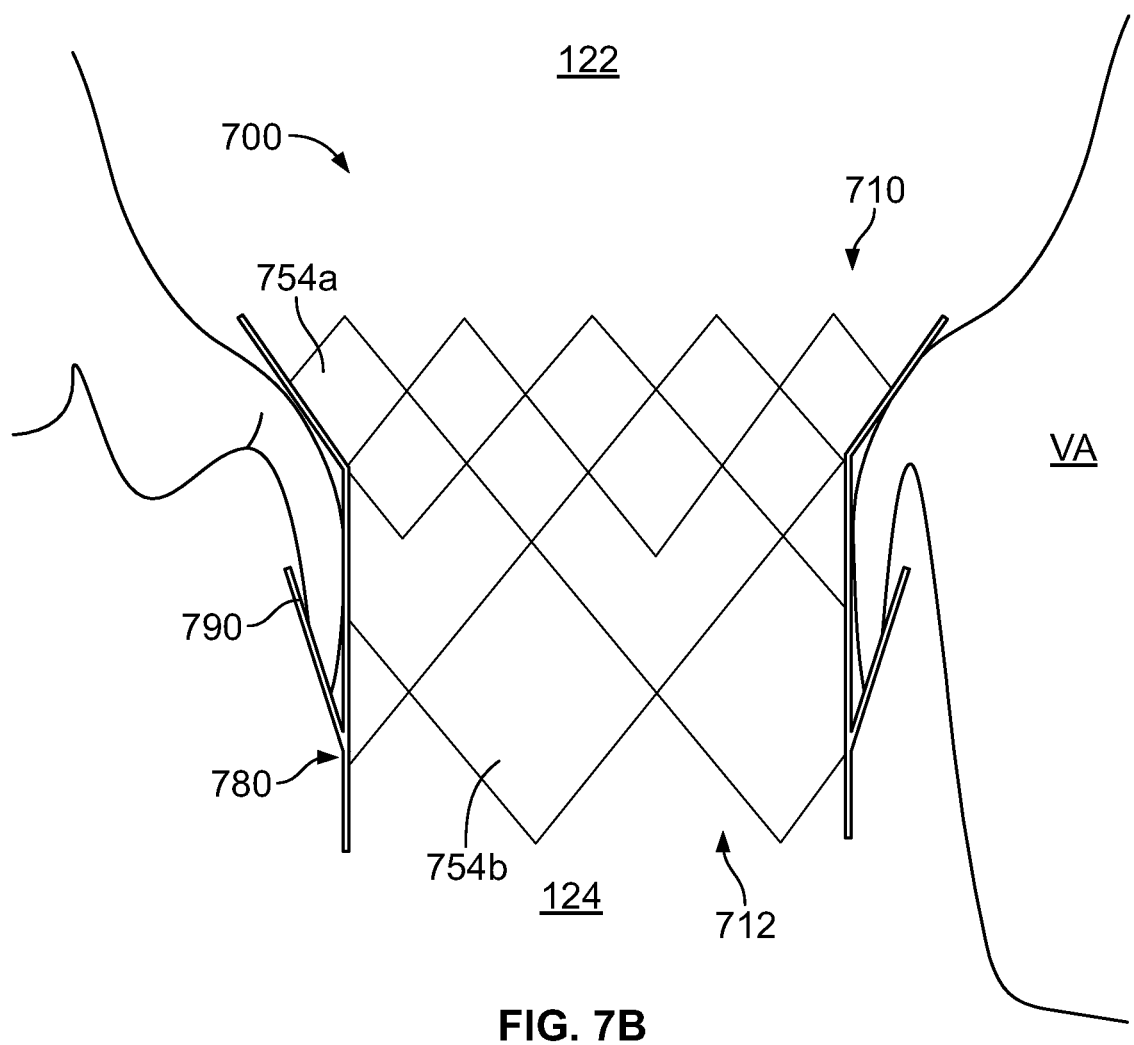
FIG. 7B is a schematic representation of the stent of FIG. 7A disposed in a native valve annulus.

Once hooks 790 are in place, the distal portion of the split sheath may be pushed distally to release flared portion 770. As it is released, flared portion 770 begins to expand on the atrial side of the native valve annulus VA. Prosthetic heart valve 700 is illustrated after full release in FIG. 7B. The inclusion of smaller cells 754*a* in a high-density arrangement in flared portion 770 allows for relatively greater tissue ingrowth and also facilitates creating and maintaining the flared shape of flared portion 770, which provides for better alignment and sealing at inflow end 710 of stent 700.

With body 780 and hooks 790 in the expanded condition, hooks 790 hook around the native anterior and posterior mitral valve leaflets, helping secure stent 700 in place. Because body 780 is generally comprised of larger cells 754*b* formed of thicker struts 752 instead of smaller cells 754*a* formed of thinner struts, body 780 is somewhat more rigid and facilitates better anchoring by hooks 790. This better anchoring may be partly due to the fact that hooks 790 are connected to body 780, and may also be formed of relatively thick struts 752 to provide additional strength. In addition, because hooks 790 point toward inflow end 710 during delivery and deployment, stent 700 may be resheathed any time prior to release of flared portion 770 into the expanded condition, for example by pushing a proximal portion of a split sheath distally before the distal portion of the split sheath is released. If a double proximal sheath were used, stent 700 could be resheathed at any time prior to release of the entire stent into the expanded condition.

Referring back to FIG. 7A, stent 700 may include one or more commissure attachment features ("CAFs") 792 and one or more retention members 794 as are known in the art. Each CAF 792 provides a site for the prosthetic valve leaflets to be attached to stent 700. Each retention member 794 provides a feature for connecting stent 700 to the delivery device, the connection being maintained until stent 700 is fully released from the delivery device. It should further be noted that, although hooks 790 are shown as being formed integrally with stent 700, hooks 790 may be formed separately of any one or a combination of a variety of materials, including for example Nitinol, polymers such as polyvinyl alcohol ("PVA"), and tissues such as bovine or porcine cardiac tissue.

Figure 7C:
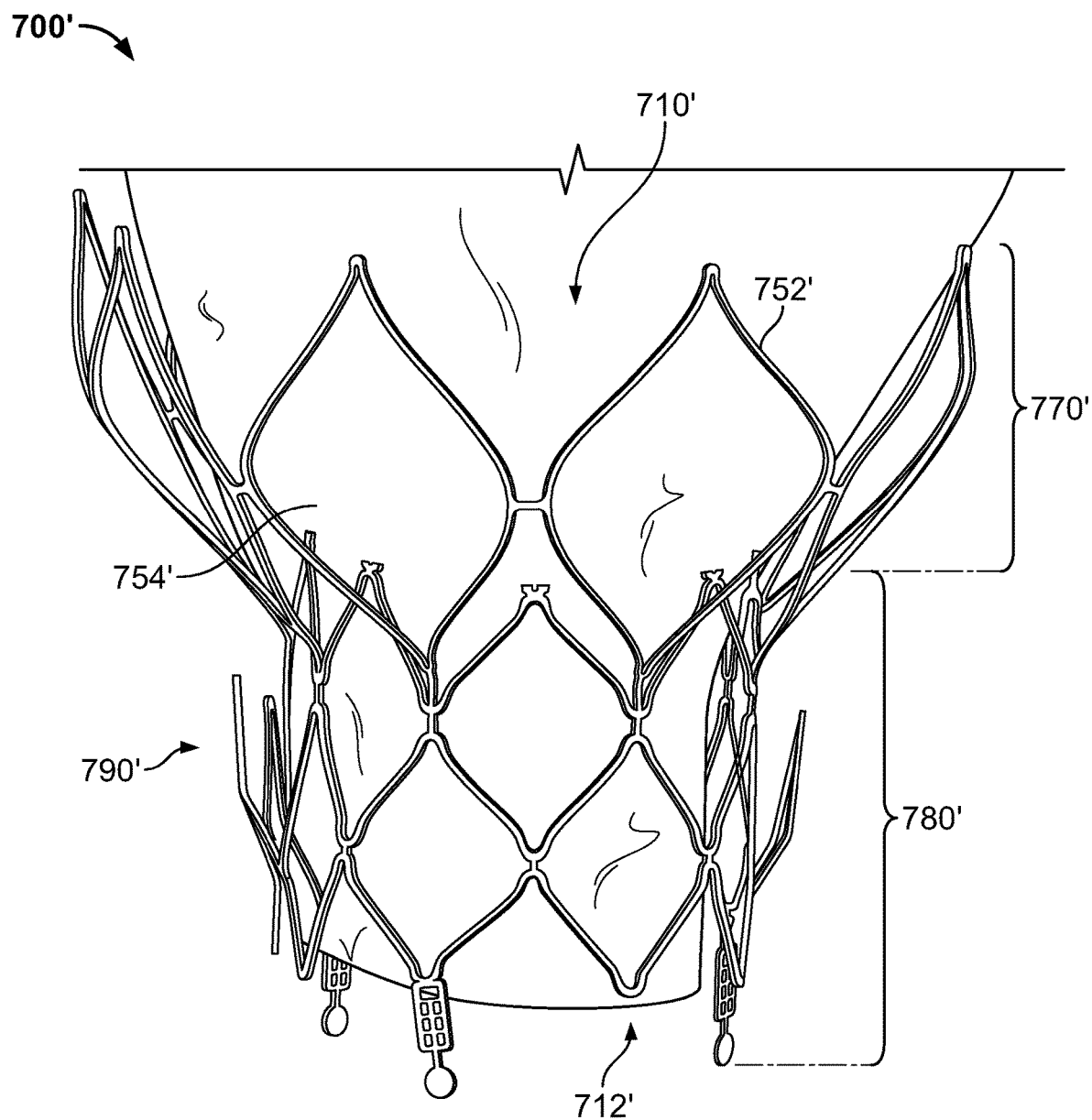
FIG. 7C is a perspective view of another stent of a prosthetic heart valve according to the present disclosure.

FIG. 7C illustrates an alternate embodiment of stent 700' of a prosthetic heart valve according to another embodiment of the disclosure. (It should be noted in FIG. 7C that an opaque strip of material is positioned within stent 700' to more clearly demonstrate features of the stent. This strip of material forms no part of stent 700' or the prosthetic valve incorporating the stent.) Stent 700' has features in common with stent 700. For example, stent 700' is collapsible and expandable, has inflow end 710' and outflow end 712', and may be formed from biocompatible materials that are capable of self-expansion. Stent 700' may include a plurality of struts 752' that form cells connected to one another in one or more annular rows around the stent. Stent 700' includes flared portion 770' at inflow end 710'. Flared portion 770' extends radially outwardly in a direction away from outflow end 712' and may include one or more circumferential rows of cells 754'. Stent 700' may also include a substantially cylindrical body 780' that extends from outflow end 712' toward inflow end 710'. Body 780' may include one or more circumferential rows of cells 754'. Each cell 754' may be formed from a group of struts 752' that defines a general diamond shape.

Figure 7D:
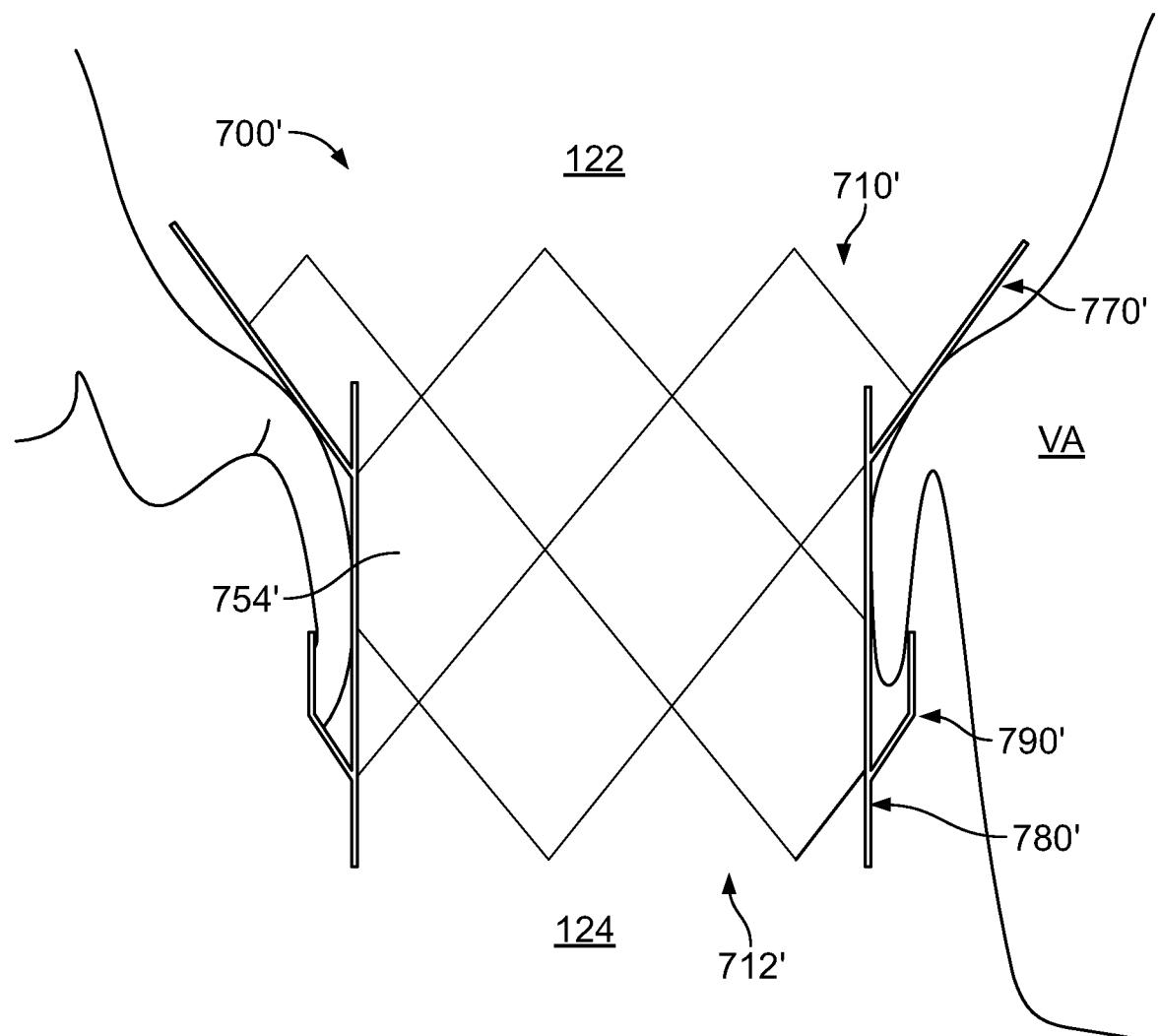
FIG. 7D is a schematic representation of the stent of FIG. 7C disposed in a native valve annulus.

Stent 700' may also include a portion with anchor members, such as hooks 790'. Hooks 790' may be formed of struts 752' that extend radially outwardly toward inflow end 710', and then angle back such that they extend generally parallel to a longitudinal axis of stent 700'. Hooks 790' may be integral with stent 700', being formed from the same single piece of starting material, and may be connected to stent 700' anywhere on body 780'. Hooks 790' may be generally similar to hooks 790 of stent 700, with at least two distinctions. First, as described above, rather than extend at a generally constant angle radially outward from body 780', hooks 790' extend at a first angle and then angle back such that a free end of each hook 790' is generally parallel to the longitudinal axis of stent 700'. As illustrated in FIG. 7D, this configuration may provide a better clamping action of native valve leaflets 136 and 138. It should be noted that the free end of hooks 790' need not be exactly parallel to the longitudinal axis and variations from parallel may exist. Second, the free end of hooks 790' may be rounded or otherwise curved. Compared to a free end with a sharp angle, hooks 790' may be less traumatic to the native tissue.

Flared portion 770' may also vary from flared portion 770 of stent 700, at least in that flared portion 770' is not connected to body 780' at the tip of a cell 754'. Rather than being connected to the portion of body 780' that is closest to inflow end 710', flared portion 770' is connected to body 780' farther toward outflow end 712'. In the illustrated embodiment, flared portion 770' is connected to body 780' at a point where two adjacent cells 754' in the same circumferential row meet. This configuration results in some overlap in the longitudinal direction of flared portion 770' and body 780'. When implanted, as illustrated in FIG. 7D, flared portion 770' makes contact with native valve annulus VA, while the points on body 780' closest to inflow end 710' extend a distance into left atrium 122. Because structures including a cuff and valve assembly (not illustrated in FIGS. 7C-D) would be attached to body 780', retaining the cylindrical geometry of body 780' near the point of contact between flared portion 770' and native valve annulus VA may help more evenly distribute the pressures and forces exerted on stent 700' during normal operation. The delivery and deployment of a prosthetic heart valve incorporating stent 700' may be substantially the same as described above in relation to stent 700.

Figure 8A:
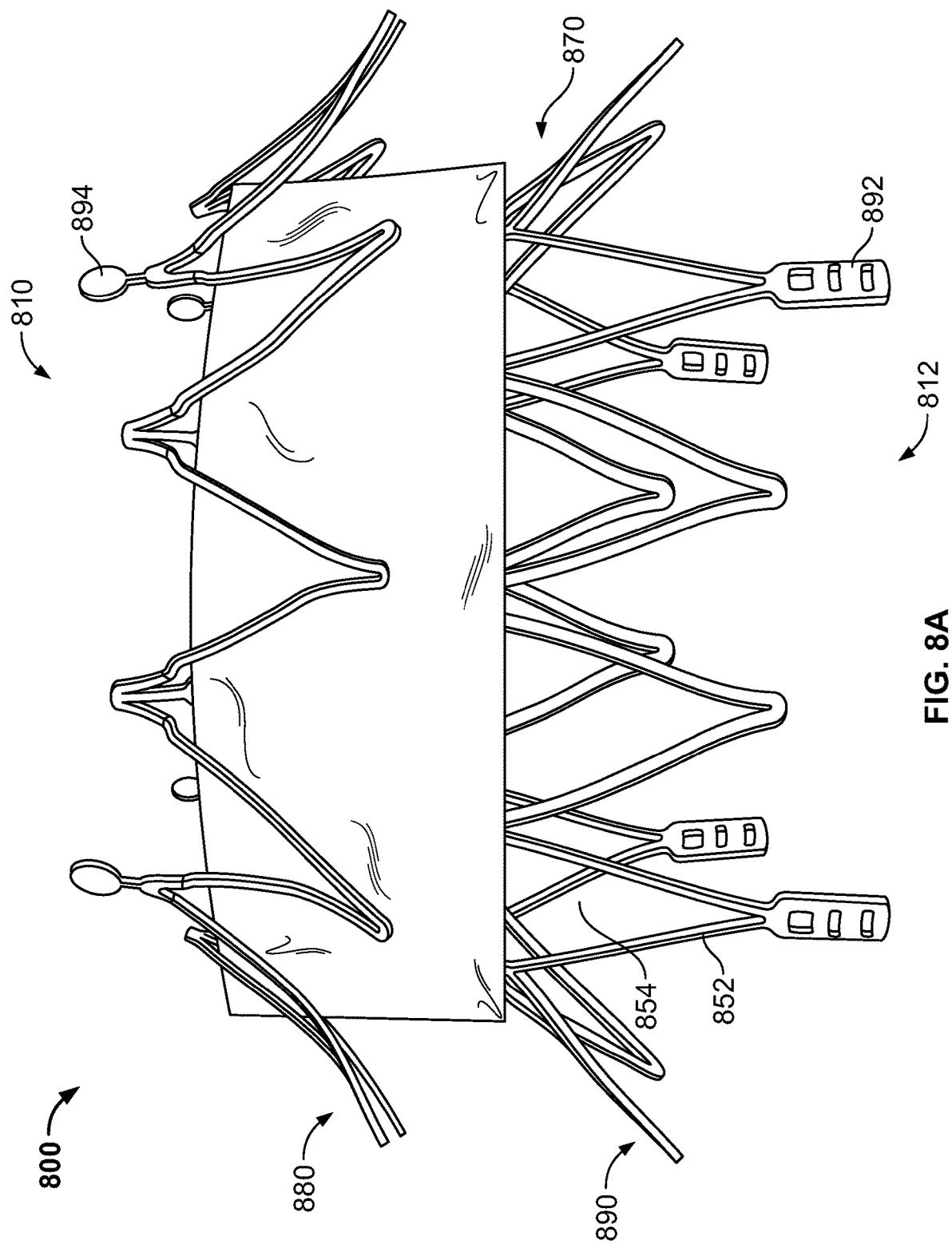
FIG. 8A is a side view of another stent of a prosthetic heart valve according to the present disclosure.

FIG. 8A illustrates a stent 800 of a prosthetic heart valve according to another embodiment of the disclosure. Stent 800 is collapsible and expandable for use in a prosthetic heart valve for replacing the function of the native mitral valve of a patient. In FIG. 8A, stent 800 is illustrated in its expanded condition.

Stent 800 has inflow end 810 and outflow end 812, and may be formed from biocompatible materials that are capable of self-expansion, such as, for example, shape memory alloys including Nitinol. Stent 800 may include a plurality of struts 852 that form cells 854 connected to one another in one or more annular rows around the stent.

Stent 800 includes a substantially cylindrical body 870 and two anchor sections. The anchor sections may take the form of a first circumferential row of hooks 880 and a second circumferential row of hooks 890. Each hook 880 in the first circumferential row has a first end attached to inflow end 810 of stent 800 and a free end extending radially outwardly and toward outflow end 812 of stent 800 in the expanded condition. (It should be noted in FIG. 8A that an opaque strip of material is positioned between first circumferential row of hooks 880 and body 870 to more clearly demonstrate their relative radial positioning. This strip of material forms no part of stent 800 or the prosthetic valve incorporating the stent.) Each hook 890 in the second circumferential row has a first end attached to body 870 of stent 800 at a spaced distance from inflow end 810 and a free end extending radially outwardly and toward outflow end 812 in the expanded condition.

When being used in a prosthetic heart valve for replacing the native mitral valve of a patient, stent 800 is crimped to a collapsed condition and positioned within a catheter or similar structure of a delivery device. In the collapsed condition, the free ends of hooks 880 in the first circumferential row and the free ends of hooks 890 in the second circumferential row all point toward outflow end 812 of stent 800. If a transfemoral or transaortic delivery route is used, once at the site of implantation, a sheath covering stent 800 may be retracted such that outflow end 812 of stent 800 expands first. As outflow end 812 of stent 800 expands and the sheath is retracted further, hooks 890 in the second circumferential row are released from constraint. Upon further retraction of the sheath, the remainder of stent 800, along with hooks 880 in the first circumferential row, are released from the constraint of the sheath and expand.

Figure 8B:
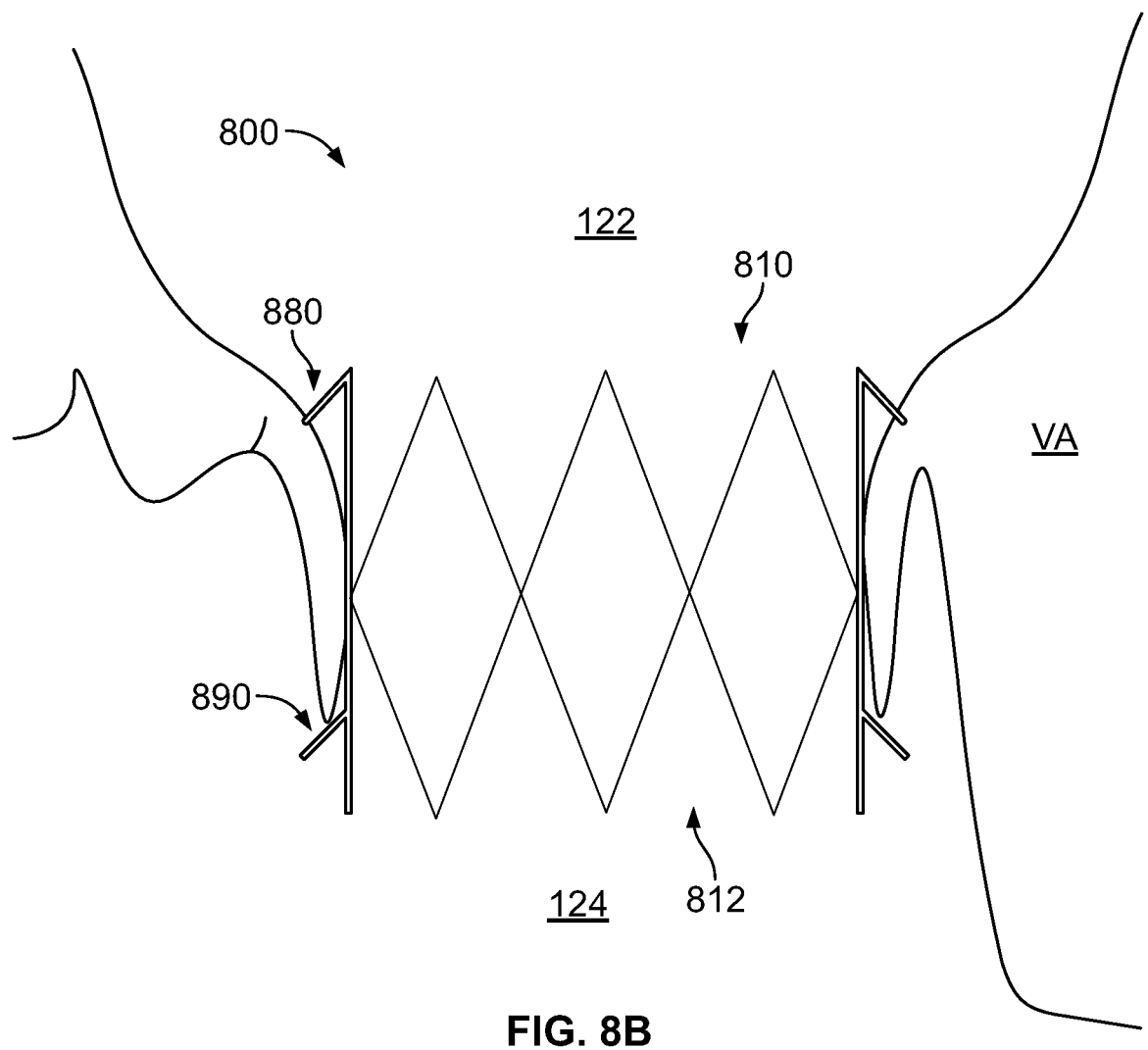
FIG. 8B is a schematic representation of the stent of FIG. 8A disposed in a native valve annulus.

FIG. 8B illustrates stent 800 in its fully expanded state within native mitral valve annuls VA. In particular, hooks 880 in the first circumferential row are positioned on, and in contact with, the atrial side of native valve annulus VA. Hooks 890 in the second circumferential row are positioned on, and in contact with, the ventricular side of native valve annulus VA. This positioning facilitates anchoring of stent 800 in native valve annulus VA, and helps to prevent PV leak.

Because the free ends of hooks 880 and 890 are all pointed toward outflow end 812 during deployment, stent 800 may be resheathed any time prior to release of the entire stent into the expanded condition. Similarly, because of this orientation of hooks 880 and 890 during deployment, the transition of hooks 880 and 890 from the collapsed condition to the expanded condition is relatively gradual, decreasing the likelihood of trauma to native valve annulus VA during release of stent 800 from the sheath. It should be understood that a similar result may be achieved with a transapical delivery route if a sheath with a distal pull-off is used. Further, other routes not specifically mentioned herein, such through the inferior vena cava, may be used with an appropriate sheath to allow the desired order of release and resheathing capabilities, as would be understood by one of ordinary skill in the art.

Referring back to FIG. 8A, stent 800 may include one or more CAFs 892 and one or more retention members 894 as are known in the art. It should be noted that retention members 894 are on inflow end 810 in this case because inflow end 810 is intended to be released at the end of deployment. This is in contrast to retention members 794 of stent 700 in FIG. 7A, which are on outflow end 712 because outflow end 712 of stent 700 is intended to be released at the end of deployment.

Figure 9:
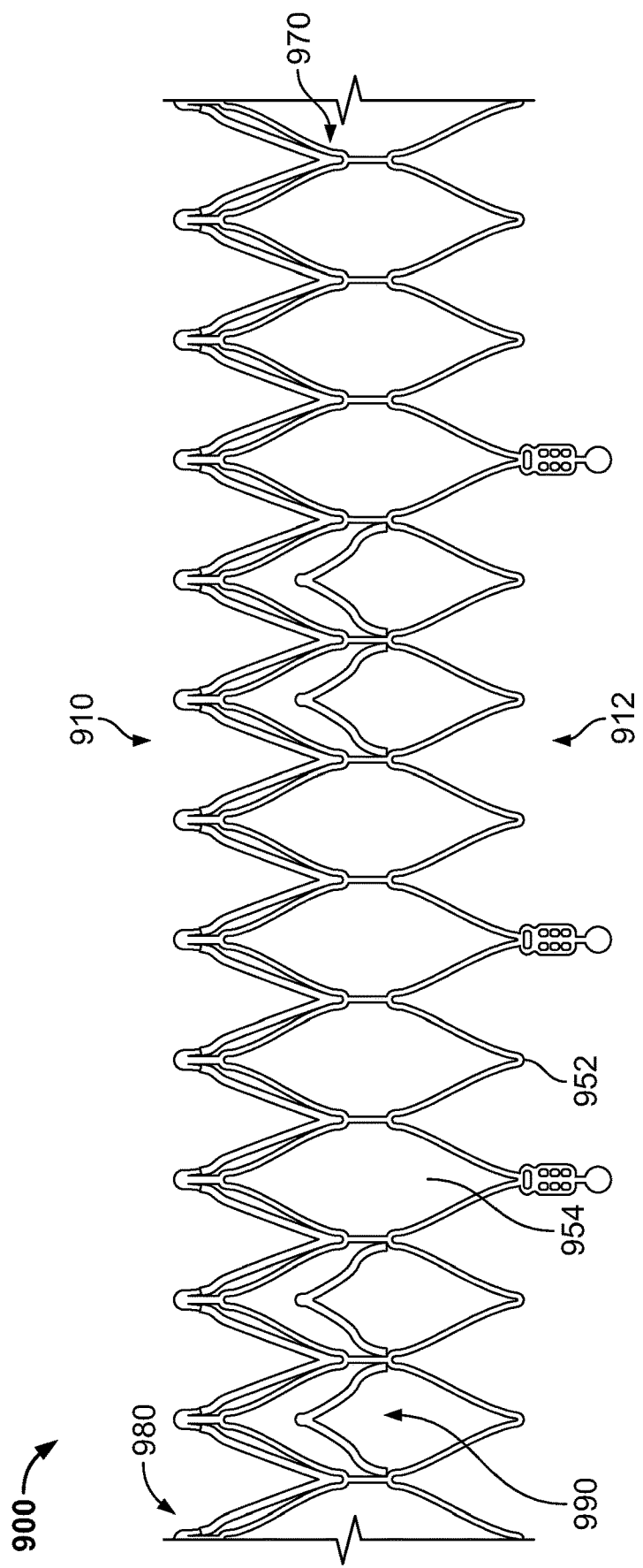
FIG. 9 is a developed view of a further stent of a prosthetic heart valve according to the present disclosure.

FIG. 9 illustrates stent 900 of a prosthetic heart valve according to a further embodiment of the disclosure. Stent 900 is collapsible and expandable for use in a prosthetic heart valve intended to replace the function of the native mitral valve of a patient. In FIG. 9, stent 900 is illustrated as if it were cut longitudinally and laid out in a flat, expanded condition.

Stent 900 has inflow end 910 and outflow end 912 and may be formed from biocompatible materials that are capable of self-expansion, such as, for example, shape memory alloys including Nitinol. Stent 900 may include a plurality of struts 952 that form cells 954 connected to one another in one or more annular rows around the stent.

Stent 900 includes a substantially cylindrical body 970 and two anchor sections. The anchor sections may take the form of a first circumferential row of hooks 980 and a second circumferential row of hooks 990. Each hook 980 in the first circumferential row has a first end attached to inflow end 910 of stent 900 and a free end extending radially outwardly and toward outflow end 912 of stent 900 when in the expanded condition. Each hook 990 in the second circumferential row has a first end attached to body 970 of stent 900 at a spaced distance from inflow end 910 and a free end extending radially outwardly and toward inflow end 910 of stent 900 when in the expanded condition. It should be noted that, when in the expanded condition, hooks 980 and 990 may extend generally perpendicular to stent body 970 or at an oblique angle towards either inflow end 910 or outflow end 912. It should also be noted that each circumferential row of hooks 980 or 990 need not be continuous. For example, groups of one, two, or more hooks 990 may be provided to anchor stent 900 to native anterior and posterior mitral valve leaflets, with a number of cells 954 without hooks 990 being positioned between the groups.

When used in a prosthetic heart valve intended to replace the native mitral valve of a patient, stent 900 is crimped to a collapsed condition and positioned within a catheter or similar structure of a delivery device. In the collapsed condition, the free ends of hooks 980 in the first circumferential row and the free ends of hooks 990 in the second circumferential row all point toward the center of stent 900. This may be particularly useful when a split sheath is being used to deploy stent 900.

Generally, a split sheath refers to a sheath that is configured to house stent 900 in a collapsed condition and a portion of the sheath housing the stent may move distally with respect to the stent while the remainder of the sheath housing the stent may remain stationary or may independently move proximally with respect to the stent. With a split sheath inflow end 910 may be exposed before or after outflow end 912. In other words, distal movement of one portion of the sheath housing will expose inflow end 910, while proximal movement of the remainder of the sheath housing will expose outflow end 912. Although hooks 980 and 990 may be deployed in any desired order, it may be preferable to first deploy second circumferential row of hooks 990 in left ventricle 124 and then push stent 900 such that hooks 990 engage native valve leaflets 136 and 138. Once engaged, and first circumferential row of hooks 980 may be deployed in left atrium 122 while keeping a portion of the distal delivery sheath covering inflow end 910. Once proper positioning is verified, the distal sheath may be pushed beyond inflow end 910 and the proximal sheath may be pulled off the outflow end 912 to fully release stent 900. When in the fully expanded condition, stent 900 may be anchored to the native mitral valve in a manner similar to that illustrated in FIG. 8B. However, unlike other embodiments described herein, the configurations of hooks 980 and 990 allow the entire stent 900 to be resheathed prior to the full release of the stent when a split sheath device is used for deployment.

Figure 10:
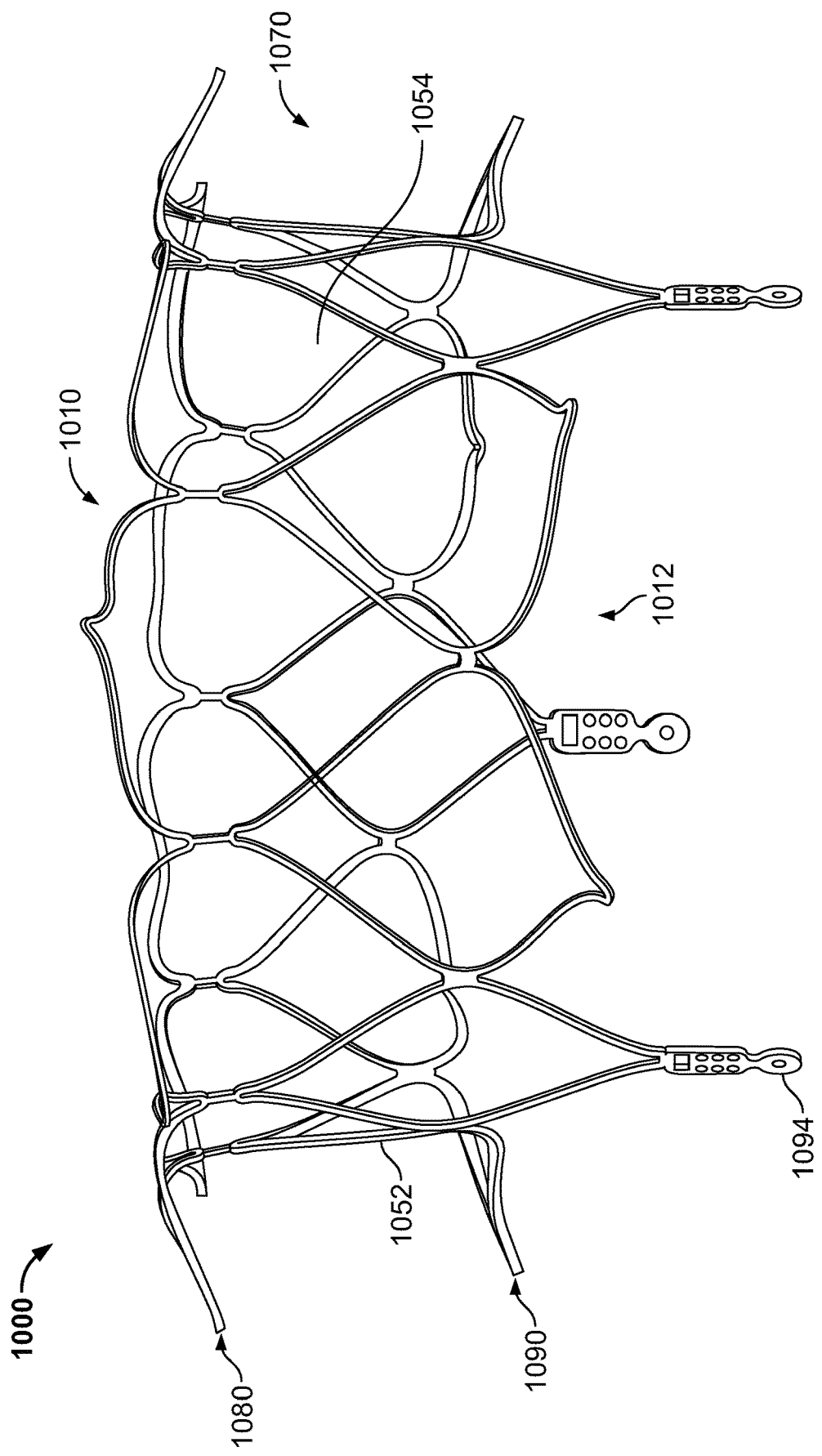
FIG. 10 is a perspective view of yet another stent of a prosthetic heart valve according to the present disclosure.

FIG. 10 illustrates a stent 1000 of a prosthetic heart valve according to a further embodiment of the disclosure. Stent 1000 is collapsible and expandable for use in a prosthetic heart valve for replacing the function of the native mitral valve of a patient. In FIG. 10, stent 1000 is illustrated in the expanded condition.

Stent 1000 has inflow end 1010 and outflow end 1012 and may be formed from biocompatible materials that are capable of self-expansion, such as, for example, shape memory alloys including Nitinol. Stent 1000 may include a plurality of struts 1052 that form cells 1054 connected to one another in one or more annular rows around the stent.

Stent 1000 includes a substantially cylindrical body 1070 and two anchor sections. The anchor sections may take the form of a first circumferential row of hooks 1080 and a second circumferential row of hooks 1090. Each hook 1080 in the first circumferential row has a first end attached to inflow end 1010 of stent 1000 and a free end extending radially outwardly. Each hook 1090 in the second circumferential row has a first end attached to outflow end 1012 of stent 1000 and a free end extending radially outwardly. In the expanded condition, hooks 1080 and 1090 may extend substantially perpendicularly to the central axis of body 1070 or, for each circumferential row, the hooks in that circumferential row may extend at an angle towards the hooks in the other circumferential row. Each hook 1080 may be a part of a single cell 1054 that is also part of body 1070. Similarly, each hook 1090 may be part of a single cell 1054 that is also part of body 1070. The first circumferential row of hooks 1080 may extend continuously around the perimeter of inflow end 1010. In other words, each cell 1054 at inflow end 1010 may form a hook 1080. However, it should be understood that hooks 1080 need not extend continuously around the perimeter of inflow end 1010 and cells 1054 not forming a hook may be interposed between cells that do form hooks. The second circumferential row of hooks 1090 is preferably not continuous. In other words, at least some cells 1054 at outflow end 1012 preferably do not from a hook 1090. For example, cells 1054 terminating in a CAF 1094 preferably do not form a hook 1090, otherwise the ability to attach a prosthetic valve to stent 1000 could be hindered.

When used in a prosthetic heart valve to replace the native mitral valve of a patient, stent 1000 is crimped to a collapsed condition and positioned within a catheter or similar structure of a delivery device. In the collapsed condition, the free ends of hooks 1080 in the first circumferential row point away from outflow end 1012 and the free ends of hooks 1090 in the second circumferential row point away from inflow end 1010.

Depending on the particular mode of delivery and sheath used to deploy stent 1000, stent 1000 may be only partially resheathable. In other words, if the hooks in only one circumferential row have been deployed from the delivery device, stent 1000 may be resheathed to reposition its associated prosthetic valve. If, on the other hand, the hooks in both circumferential rows have been deployed from the delivery device, stent 1000 may no longer be resheathed even if retention members 1094 are still connected to the delivery device. Despite being only partially resheathable, the configuration of stent 1000 may provide a number of benefits. For example, stent 1000 generally has a less complex structure than, for example, stents 700, 800, and 900, which may result in simplified manufacturing. Also, at least partly because hooks 1080 and 1090 are portions of cells 1054 of body 1070, all cells 1000 of stent 1050 may be arranged in a high-density format. The high-density format may provide, for example, a greater surface area of material to interact with the native anatomy as well as for supporting a cuff, valves, and/or sealing materials attached thereto. In addition, when in the crimped condition, there is no overlap between either row of hooks and cylindrical body 1070, permitting a smaller crimp profile to be obtained. Similarly to stents 700, 800, and 900, once stent 1000 is properly positioned in native valve annulus VA, hooks 1080 and 1090 may function to both anchor stent 1000 in place and to help seal against PV leak.

Figure 11:
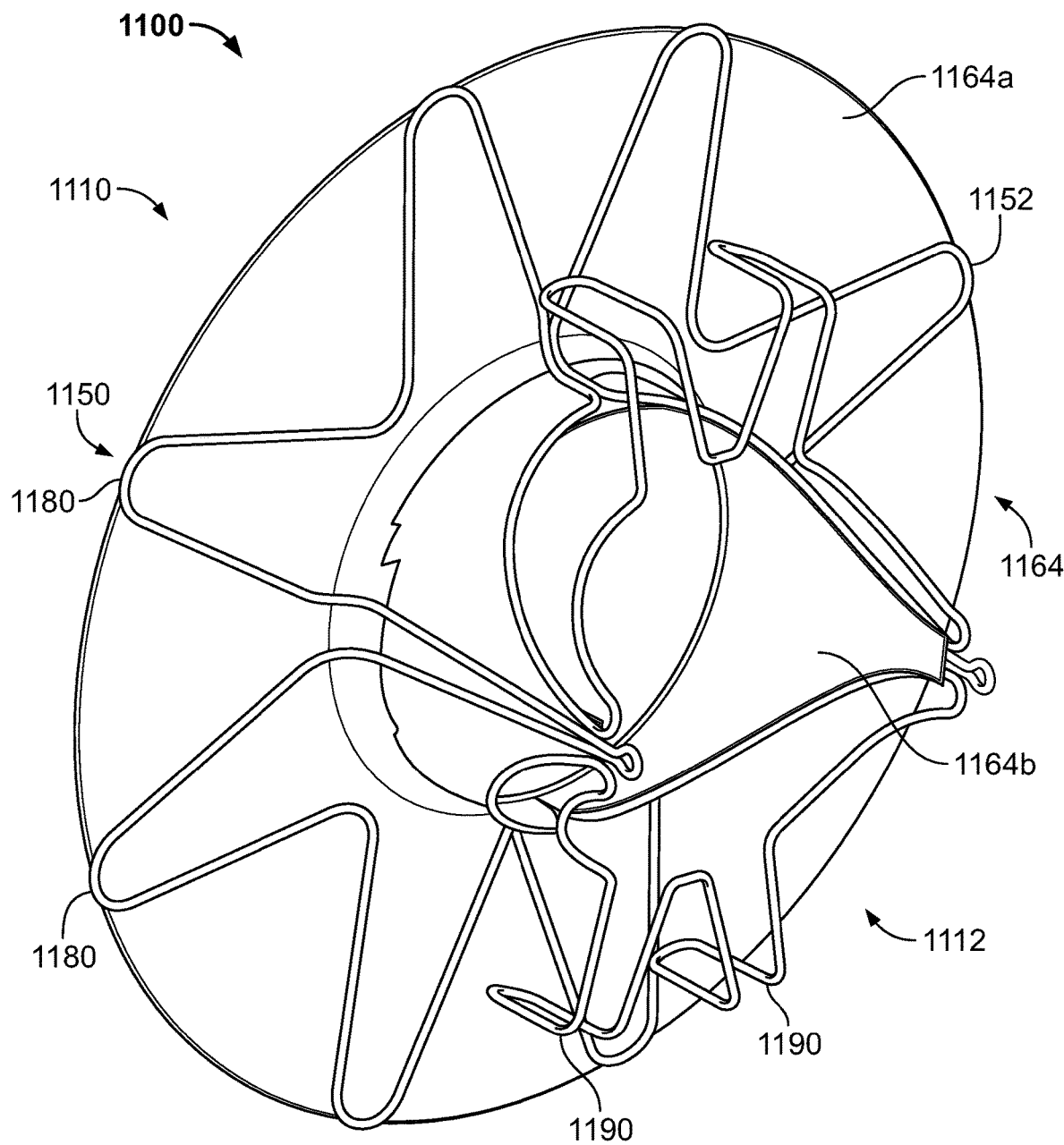
FIG. 11 is a perspective view of another prosthetic heart valve according to the present disclosure.

FIG. 11 illustrates a prosthetic heart valve 1100 according to another embodiment of the disclosure. Prosthetic heart valve 1100 is collapsible and expandable and designed to replace the function of the native mitral valve of a patient. In FIG. 11, prosthetic heart valve 1100 is illustrated in the expanded condition.

Prosthetic heart valve 1100 may include wire-form stent 1150, which may be formed from biocompatible materials that are capable of self-expansion, such as, for example, shape memory alloys including Nitinol. Unlike other embodiments described herein, stent 1150 may be formed from a single wire 1152 shaped as desired, as opposed to, for example, a single tube laser cut to a desired shape. In the illustrated embodiment, stent 1150 includes two anchor sections. In particular, the anchor sections may include a first series of hooks 1180 and a second series of hooks 1190. Each hook 1180 in the first series may extend radially outward from inflow end 1110 of stent 1150. Each hook 1190 in the second series may extend radially outward from outflow end 1112 of stent 1150. A free end of each hook 1190 may be bent back toward inflow end 1110.

Prosthetic heart valve 1100 may include a cuff 1164 attached to stent 1150. Cuff 1164 may include a first generally flat portion 1164a that spans across and is attached to first series of hooks 1180. Preferably, hooks 1180 extend substantially in a continuous pattern around the circumference of prosthetic heart valve 1100 to provide adequate support for first cuff portion 1164a. When prosthetic heart valve 1100 is implanted, first cuff portion 1164a is positioned on the atrial side of the native valve annulus and may act as a sealing member similar to sealing members 480 and 580 of prosthetic heart valves 400 and 500, respectively. Cuff 1164 may include a second portion 1164b projecting from flat portion 1164a in the form of an annular wall surrounding an opening generally in the center of the flat portion. Second portion 1164b provides structure for the attachment of prosthetic leaflets to prosthetic heart valve 1100. When prosthetic heart valve 1100 is implanted, second series of hooks 1190 may be positioned on the ventricular side of the native mitral valve annulus, and may hook around the native mitral valve leaflets to provide anchoring for prosthetic heart valve 1100. With this configuration, two groups of hooks 1190 corresponding to the positions of native mitral valve leaflets may be sufficient for anchoring, without needing hooks 1190 to extend around the entire circumference of stent 1150.

While prosthetic leaflets may be attached to cuff 1164 and stent 1150 to form a fully functioning prosthetic heart valve, cuff 1164 and stent 1150 may be used in combination as a docking station in a two-step delivery system, similar to docking station 600 described above. If used as a docking station, cuff 1164 and stent 1150 may be implanted in the native valve annulus first, followed by the implantation of a traditional prosthetic heart valve or any prosthetic heart valve described herein.

Figure 12:
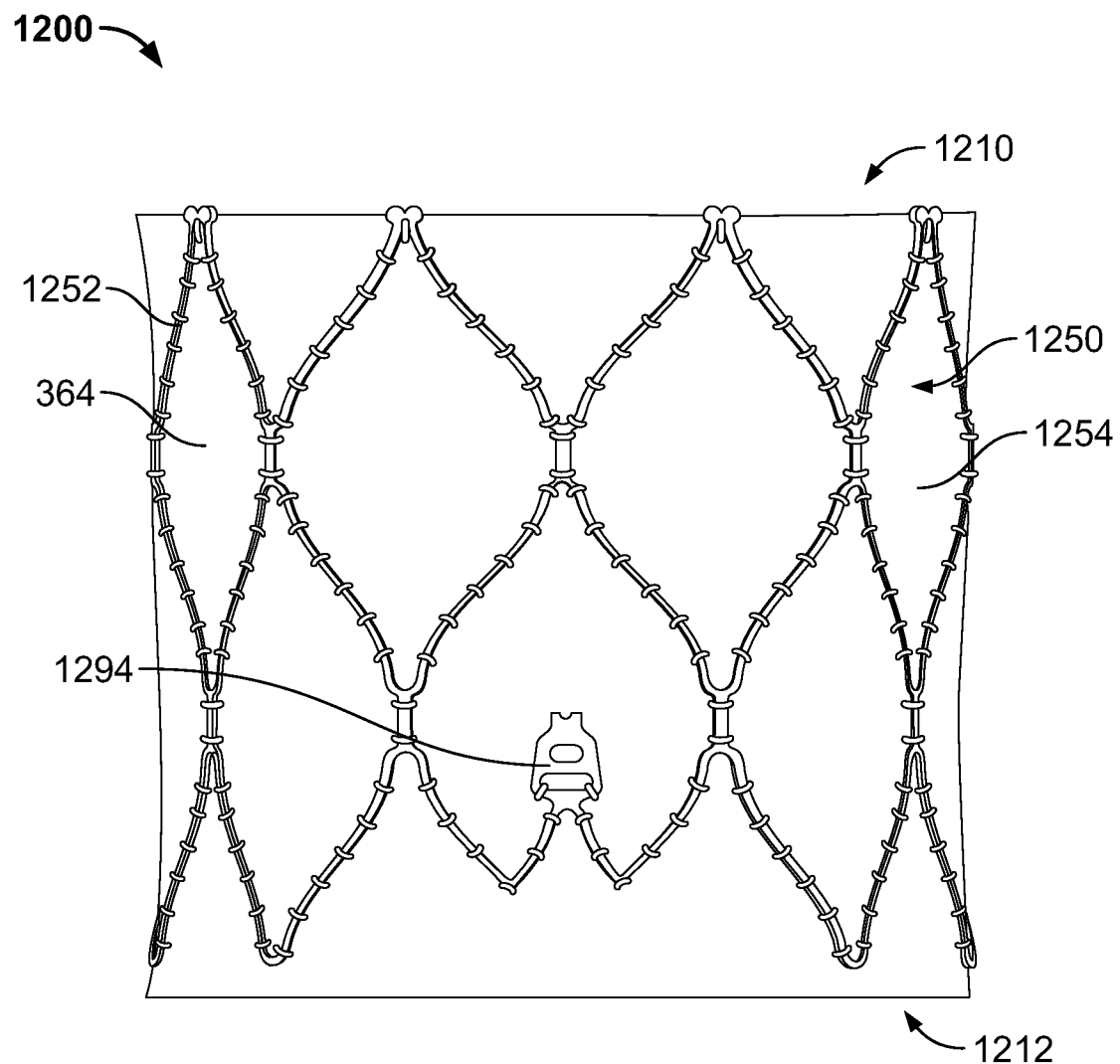
FIG. 12 is a side view of a further prosthetic heart valve according to the present disclosure.

FIG. 12 is a side view of prosthetic heart valve 1200 according to a further embodiment of the disclosure. Prosthetic heart valve 1200 is a collapsible prosthetic heart valve designed to replace the function of the native mitral valve of a patient. Prosthetic valve 1200 may be substantially cylindrical, with inflow end 1210 and outflow end 1212. When used to replace native mitral valve 130, prosthetic valve 1200 may have a low profile so as not to interfere with atrial function in the native valve annulus.

Prosthetic heart valve 1200 may include stent 1250, which may be formed from biocompatible materials that are capable of self-expansion, such as, for example, shape memory alloys including Nitinol. Stent 1250 may include a plurality of struts 1252 that form cells 1254 connected to one another in one or more annular rows around the stent.

Prosthetic heart valve 1200 may also include a valve assembly similar to that described in connection with FIGS. 3A-B. The prosthetic leaflets of the valve assembly replace the function of native mitral valve leaflets 136 and 138. That is, the leaflets coapt with one another to function as a one-way valve. The prosthetic leaflets may be attached to stent 1250 at one or more CAFs 1294. Each CAF 1294 may be integral with stent 1250, for example by laser cutting the entire structure from a tube of material.

For prosthetic mitral valves, the stents generally include CAFs that extend in the outflow direction and which are connected to a cell at the outflow end of the stent. In other words, CAFs are generally positioned at an end of the stent. Due to this positioning, and due to the fact that the prosthetic leaflets are attached to the CAFs and are subjected to forces, for example from restricting blood flow in the retrograde direction, the CAFs are prone to deflect inwardly at times during normal operation. This is particularly true when the mitral valve is closed and the pressure in the left ventricle is greater than the pressure in the left atrium.

As illustrated in FIG. 12, CAF 1294 is embedded within a cell 1254 of stent 1250, rather than being positioned beyond outflow end 1212. In other words, CAF 1294 is positioned between inflow end 1210 and outflow end 1212. CAF 1294 has a first end attached to struts 1252 and a second free end pointing toward inflow end 1210. This configuration may reduce the torque experienced by CAF 1294 due to the forces acting on the prosthetic leaflets attached to CAF 1294, thereby reducing the deflection of CAF 1294 during normal operation. This, in turn, may result in better coaptation between the prosthetic leaflets and less deterioration of the valve.

As illustrated in FIG. 12, CAF 1294 is embedded within a cell 1254 of stent 1250, rather than being positioned beyond outflow end 1212. In other words, CAF 1294 is positioned between inflow end 1210 and outflow end 1212. CAF 1294 has a first end attached to struts 1252 and a second free end pointing toward inflow end 1210. This configuration may reduce the torque experienced by CAF 1294 due to the forces acting on the prosthetic leaflets attached to CAF 1294, thereby reducing the deflection of CAF 1294 during normal operation. This, in turn, may result in better coaptation between the prosthetic leaflets and less deterioration of the valve.

Figure 13:
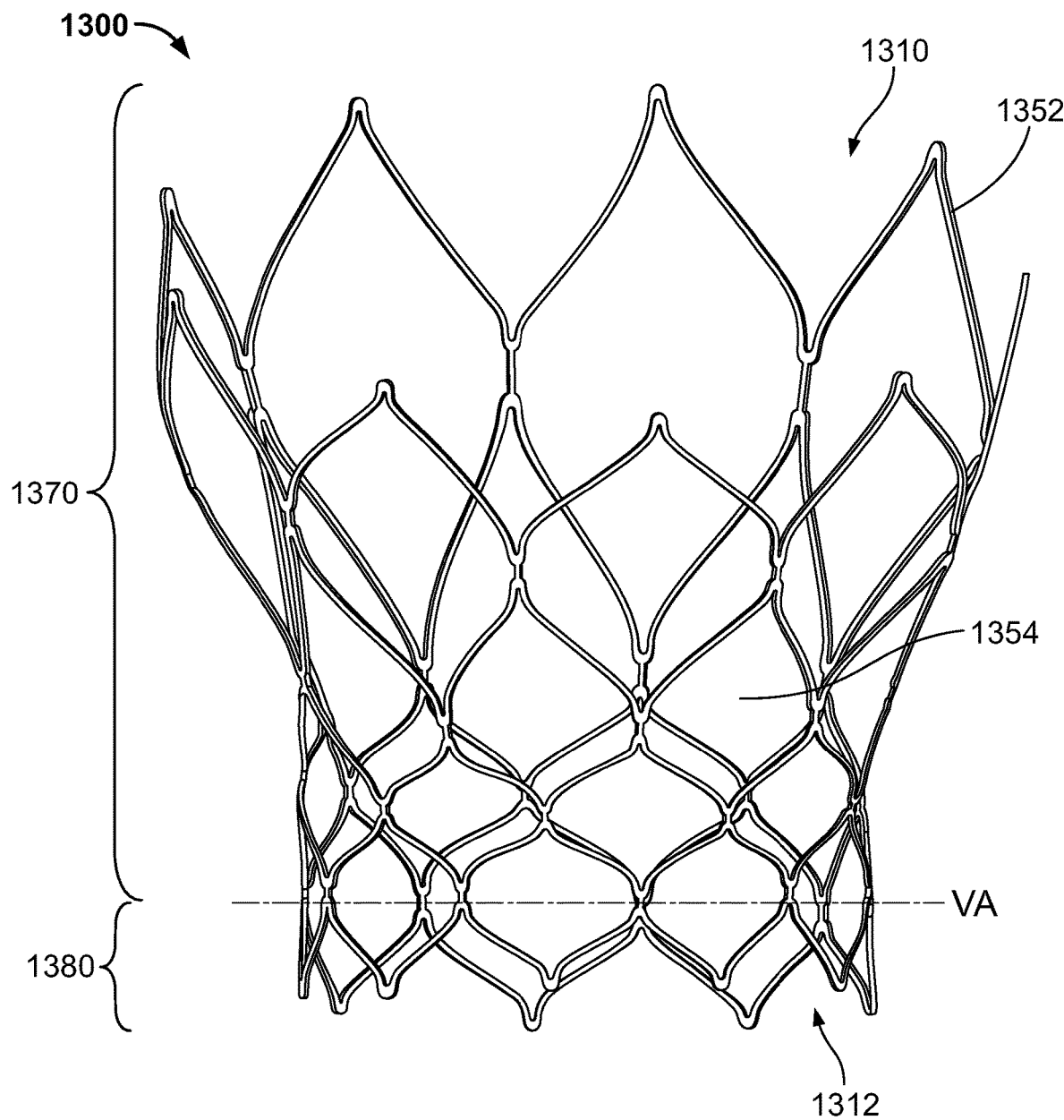
FIG. 13 is a perspective view of still another stent of a prosthetic heart valve according to the present disclosure.

FIG. 13 illustrates a stent 1300 of a prosthetic heart valve according to still another embodiment of the disclosure. Stent 1300 is collapsible and expandable for use in a prosthetic heart valve intended to replace the function of the native mitral valve of a patient. In FIG. 13, stent 1300 is illustrated in its expanded condition.

Stent 1300 has inflow end 1310 and outflow end 1312, and may be formed from biocompatible materials that are capable of self-expansion, such as, for example, shape memory alloys including Nitinol. Stent 1300 may include a plurality of struts 1352 that form cells 1354 connected to one another in one or more annular rows around stent 1300.

Stent 1300 may be thought of as having an atrial portion 1370 and a ventricular portion 1380. When implanted in native valve annulus VA, atrial portion 1370 of stent 1300 is positioned on the atrial side of native valve annulus VA, while ventricular portion 1380 of stent 1300 is positioned on the ventricular side of native valve annulus VA. Atrial portion 1370 of stent 1300 has a generally bulbous shape and is configured to protrude farther into left atrium 122 than ventricular portion 1380 protrudes into left ventricle 124. The bulbous shape of atrial portion 1370 provides anchoring of stent 1300, helping to resist the migration of the stent into left ventricle 124. The bulbous shape of atrial portion 1370 and the extent of anchoring in left atrium 122 reduce the radial forced needed at native valve annulus VA to keep stent 1300 in place. As a result, ventricular portion 1380 need only extend minimally into left ventricle 124, which may reduce interference with chordae tendineae 134. For example, as illustrated, less than a full row of cells 1354 is configured to be positioned in left ventricle 124 when stent 1300 is implanted in native valve annulus VA.

Various modifications may be made to the embodiments disclosed herein without departing from the scope of the disclosure. For example, although stents and prosthetic heart valves are generally described for replacement of the mitral other bicuspid valves, variations may be made to these devices to replace tricuspid valves. Thus, the prosthetic valves may be provided with three leaflets, or more or less leaflets as desired. Similarly, although generally described as self-expanding prosthetic heart valves or stents, the principles described herein are also applicable to prosthetic valves that are not self-expanding, such as balloon expandable prosthetic valves.

According to one embodiment of the disclosure, a prosthetic heart valve comprises: a stent having an inflow end, an outflow end, a center portion between the inflow end and the outflow end, a collapsed condition, and an expanded condition; a collapsible and expandable valve assembly disposed within the stent and having a plurality of leaflets; a first annular sealing member coupled to the inflow end; and a second annular sealing member coupled to the outflow end; and/or the first and second sealing members each have a diameter greater than a diameter of the stent when the stent is in the expanded condition; and/or the stent is substantially cylindrical in the expanded condition; and/or the first sealing member has a substantially planar configuration when the stent is in the expanded condition; and/or the inflow end and the outflow end of the stent each has a diameter greater than a diameter of the center portion of the stent when the stent is in the expanded condition; and/or the first sealing member is substantially nonplanar when the stent is in the expanded condition; and/or an outer perimeter of the first sealing member is closer to the outflow end than an inner perimeter of the first sealing member when the stent is in the expanded condition.

According to another embodiment of the disclosure, a stent having an expanded condition and a collapsed condition comprises: a substantially cylindrical body having a first end and a second end; a flared portion coupled to the first end of the body and extending radially outwardly from the body and away from the second end of the body when the stent is in the expanded condition; and a plurality of anchor members each having a first end coupled to the body and a second free end extending radially outwardly from the body and toward the first end of the body when the stent is in the expanded condition, wherein the flared portion and the second free ends of the anchor members are configured to extend away from the second end of the body when the stent is in the collapsed condition; and/or the flared portion and the body are each formed of a plurality of struts that form cells having an area, the area of each cell of the body being greater than the area of each cell of the flared portion when the stent is in the expanded condition; and/or the flared portion and the body are each formed of a plurality of struts having a thickness, the thickness of the struts forming the flared portion being less than the thickness of the struts forming the body.

According to a further embodiment of the disclosure a stent having an expanded condition and a collapsed condition comprises: a substantially cylindrical center body having a first end and a second end; a first plurality of anchor members each having a first end coupled to the first end of the body and a second free end extending radially outwardly from the body and toward the second end of the body when the stent is in the expanded condition; and a second plurality of anchor members each having a first end coupled to the body and a second free end extending radially outwardly from the body and toward the second end of the body when the stent is in the expanded condition, wherein the first and second plurality of anchor members are configured to extend toward the second end of the body when the stent is in the collapsed condition.

According to still another embodiment of the disclosure, a stent having an expanded condition and a collapsed condition comprises: a substantially cylindrical center body having a first end and a second end; a first plurality of anchor members each having a first end coupled to the body and a second free end extending radially outwardly from the body and toward the first end of the body when the stent is in the expanded condition; and a second plurality of anchor members each having a first end coupled to the first end of the body and a second free end extending radially outwardly from the body and toward the second end of the body when the stent is in the expanded condition, wherein the first plurality of anchor members extend toward the first end of the body and the second plurality of anchor members extend toward the second end of the body when the stent is in the collapsed condition; and/or the second plurality of anchor members includes a first group of anchor members and a second group of anchor members, the first group being configured to engage a native posterior mitral valve leaflet and the second group being configured to engage a native anterior mitral valve leaflet when the stent is implanted in a native mitral valve annulus of a patient.

According to yet another embodiment of the disclosure, a stent having an expanded condition and a collapsed condition comprises: a substantially cylindrical center body having a first end, a second end, and a longitudinal axis extending between the first end and the second end; a first plurality of anchor members each having a first end coupled to the body and a second free end extending radially outwardly from the body and substantially perpendicular to the longitudinal axis of the body when the stent is in the expanded condition; and a second plurality of anchor members each having a first end coupled to the body and a second free end extending radially outwardly from the body and substantially perpendicular to the longitudinal axis of the body when the stent is in the expanded condition, wherein the first plurality of anchor members extend away from the second end of the body and the second plurality of anchor members extend away from the first end of the body when the stent is in the collapsed condition; and/or a plurality of struts forming a first circumferential row of cells and a second circumferential row of cells, wherein each of the first plurality of anchor members is at least partially formed from one of the cells in the first circumferential row and each of the second plurality of anchor members is at least partially formed from one of the cells in the second circumferential row.

According to yet a further embodiment of the disclosure, a prosthetic heart valve comprises: a stent having an inflow end, an outflow end, a collapsed condition, and an expanded condition, the stent being formed from wire and having a first series of hooks and a second series of hooks; and a cuff coupled to the stent, wherein, when the stent is in the expanded condition, each hook of the first series extends radially outwardly from the stent at the inflow end and each hook of the second series includes a first portion that extends radially outwardly from the stent at the outflow end and a second portion that extends toward the inflow end; and/or the cuff has a first substantially flat portion that spans across and is coupled to the first series of hooks.

According to an even further embodiment of the disclosure, a prosthetic heart valve comprises: a stent having an inflow end, an outflow end, a collapsed condition, and an expanded condition, the stent being formed of a plurality of struts; a collapsible and expandable valve assembly disposed within the stent and having a plurality of leaflets; and a commissure attachment feature attached to at least one of the plurality of struts and positioned between the inflow end and the outflow end when the stent is in the expanded condition; and/or the commissure attachment feature has a first end attached to at least one of the plurality of struts and a second free end extending toward the inflow end when the stent is in the expanded condition.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic mitral valve system comprising:
a hollow tube having an inflow end, an outflow end, and a center portion extending between the inflow end and the outflow end, the hollow tube having a first anchor rim at the inflow end of the hollow tube and a second anchor rim at the outflow end of the hollow tube, the first anchor rim extending radially outwardly from the center portion and adapted to engage an atrial side of a native mitral valve annulus, the second anchor rim extending radially outwardly from the center portion and adapted to engage a ventricular side of the native mitral valve annulus, wherein the center portion is sized to engage the mitral valve annulus and is substantially cylindrical;
a collapsible and self-expandable prosthetic heart valve assembled to and received within the hollow tube, the collapsible and self-expandable prosthetic heart valve including a stent and a valve assembly having a plurality of prosthetic leaflets coupled to the stent at commissure attachment features of the stent, the commissure attachment features of the stent being positioned exclusively at an outflow end of the stent,
wherein the collapsible and self-expandable prosthetic heart valve is configured to be assembled to the hollow tube after the hollow tube is implanted into the native mitral valve,
wherein the first anchor rim has a cylindrical outer surface that is concentric with the center portion of the hollow tube, and
wherein the second anchor rim has a cylindrical outer surface that is concentric with the center portion of the hollow tube.

2. The prosthetic mitral valve system of claim 1, wherein the hollow tube is self-expandable.

3. The prosthetic mitral valve system of claim 2, wherein the hollow tube is formed of Nitinol.

4. The prosthetic mitral valve system of claim 2, wherein the stent of the collapsible and self-expandable prosthetic heart valve is substantially cylindrical in an expanded condition of the stent.

5. The prosthetic mitral valve system of claim 1, wherein the commissure attachment features are integral with the stent.

6. The prosthetic mitral valve system of claim 1, wherein a first end surface of the first anchor rim is coextensive with the inflow end of the hollow tube, the first end surface lying in a plane perpendicular to a longitudinal axis of the center portion.

7. The prosthetic mitral valve system of claim 6, wherein a second end surface of the first anchor rim is inclined at an oblique angle relative to the longitudinal axis of the center portion.

8. The prosthetic mitral valve system of claim 7, wherein a first end surface of the second anchor rim is coextensive with the outflow end of the hollow tube, the second end surface lying in a plane perpendicular to the longitudinal axis of the center portion.

9. The prosthetic mitral valve system of claim 8, wherein a second end surface of the second anchor rim is inclined at an oblique angle relative to the longitudinal axis of the center portion.

10. The prosthetic mitral valve system of claim 1, wherein the first anchor rim is adapted to prevent the prosthetic mitral valve system from migrating toward the ventricular side of the native mitral valve annulus when the first anchor rim engages the atrial side of the native mitral valve annulus.

11. The prosthetic mitral valve system of claim 10, wherein the second anchor rim is adapted to prevent the prosthetic mitral valve system from migrating toward the atrial side of the native mitral valve annulus when the second anchor rim engages the ventricular side of the native mitral valve annulus.

12. The prosthetic mitral valve system of claim 1, wherein the valve assembly further includes a cuff.

13. The prosthetic mitral valve system of claim 1, wherein the valve assembly is substantially cylindrical.

14. The prosthetic mitral valve system of claim 1, wherein the valve assembly is secured to the stent via sutures.

15. The prosthetic mitral valve system of claim 1, wherein the hollow tube is a docking station adapted to be implanted into the native mitral valve annulus before the collapsible and prosthetic heart valve is assembled to the docking station.

* * * * *